US009255875B2

(12) United States Patent
Denenberg et al.

(10) Patent No.: US 9,255,875 B2
(45) Date of Patent: Feb. 9, 2016

(54) METHOD AND APPARATUS FOR INSPECTION OF CORROSION AND OTHER DEFECTS THROUGH INSULATION

(71) Applicant: Jentek Sensors, Inc., Waltham, MA (US)

(72) Inventors: Scott A. Denenberg, Boston, MA (US); Todd A. Dunford, Amherst, MA (US); Neil J. Goldfine, Newton, MA (US); Yanko K. Sheiretov, Waltham, MA (US)

(73) Assignee: Jentek Sensors, Inc., Waltham, MA (US)

( * ) Notice: Subject to any disclaimer, the term of this patent is extended or adjusted under 35 U.S.C. 154(b) by 596 days.

(21) Appl. No.: 13/660,914

(22) Filed: Oct. 25, 2012

(65) Prior Publication Data

US 2013/0124109 A1    May 16, 2013

Related U.S. Application Data

(60) Provisional application No. 61/551,232, filed on Oct. 25, 2011, provisional application No. 61/600,355, filed on Feb. 17, 2012.

(51) Int. Cl.
*G01N 17/04* (2006.01)
*G01R 33/12* (2006.01)
*G06F 17/00* (2006.01)
*G01N 27/90* (2006.01)

(52) U.S. Cl.
CPC .............. *G01N 17/04* (2013.01); *G01N 27/902* (2013.01); *G06F 17/00* (2013.01)

(58) Field of Classification Search
CPC ....... G01N 27/00; G01N 27/20; G01N 27/72; G01N 27/82; G01N 27/90; G01N 27/902; G01N 27/9033; G01N 27/904; G01N 17/00; G01N 17/006; G01N 17/04; G01N 2291/2634; G01N 21/952; G01R 33/00; G01R 33/04; G01R 33/092; G01R 33/12; G01R 33/1223; G01R 27/08; G06F 17/00
See application file for complete search history.

(56) References Cited

U.S. PATENT DOCUMENTS

| | | | |
|---|---|---|---|
| 5,453,689 A | 9/1995 | Goldfine et al. | |
| 6,992,482 B2 | 1/2006 | Shay et al. | |
| 2001/0054894 A1* | 12/2001 | Goldfine et al. | 324/207.17 |
| 2012/0013334 A1 | 1/2012 | Sheiretov et al. | |

* cited by examiner

*Primary Examiner* — Toan Le
(74) *Attorney, Agent, or Firm* — Hamilton, Brook, Smith & Reynolds, P.C.

(57) ABSTRACT

Detection of corrosion and other defects in piping is needed to prevent catastrophic pipeline failure. Sensors, systems and methods are provided to enable detection of such defects. These apparatus and methods are configured to characterize pipe protected by insulation and conductive weather protection. The sensors may utilize inductive and/or solid state sensing element arrays operated in a magnetic field generated in part by a drive winding of the sensor. Multiple excitation frequencies are used to generate the magnetic field and record corresponding sensing element responses. Relatively high excitation frequencies may be used to estimate the properties of the weather protection and sensor lift-off while lower frequencies may be used to detect internal and external pipe damage. Linear arrays may be moved to generate damage images of the pipe providing size and location information for defects. Two dimensional sensor arrays may be used to provide imaging without moving the sensor.

20 Claims, 17 Drawing Sheets

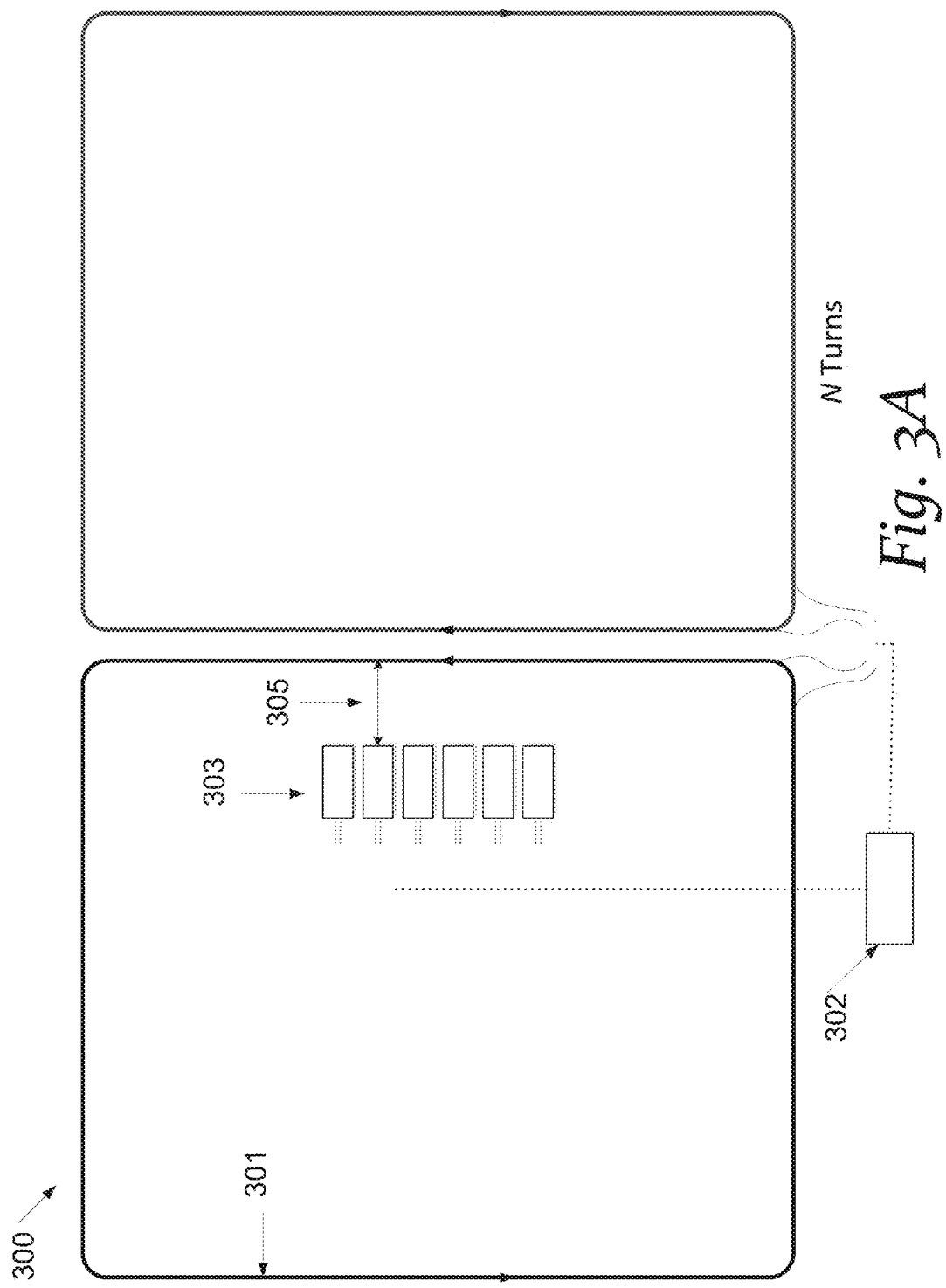

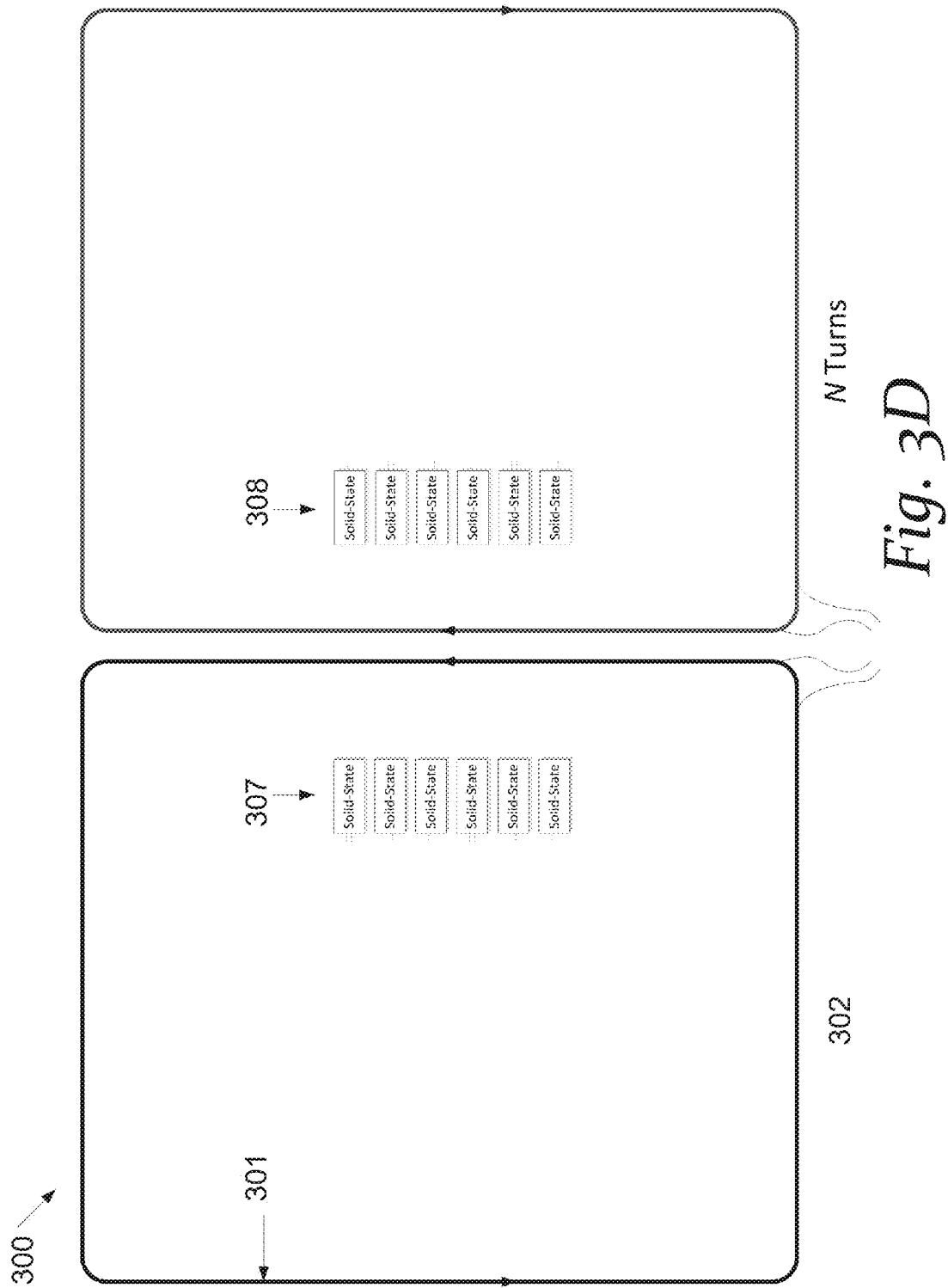

METHOD AND APPARATUS FOR INSPECTION OF CORROSION AND OTHER DEFECTS THROUGH INSULATION

The present application claims priority under 35 U.S.C. §119(e) to U.S. provisional patent application, U.S. Ser. No. 61/551,232, filed Oct. 25, 2011, which is herein incorporated by reference in its entirety. The present application claims priority under 35 U.S.C. §119(e) to U.S. provisional patent application, U.S. Ser. No. 61/600,355, filed Feb. 17, 2012.

GOVERNMENT SUPPORT

This invention was made with government support under DTPH56-10-T-00 from Department of Transportation (DOT). The government has certain rights in the invention.

BACKGROUND

Pipes used for oil, gas, and chemical transportation or as part of a refinery or processing facility may be covered by coating that can be over four inches thick. Some coatings provide thermal insulation to minimize heat transfer between the surroundings and the hot or cold materials inside of the pipe. Other coatings are applied to decrease the buoyancy of the pipe, such as a concrete weight coat for underwater pipes, or to protect the pipe from mechanical damage.

To protect thermal insulation from mechanical damage, an aluminum or stainless steel weather protection (or sometimes called a "weather jacket") may be secured over the insulation and held in place by metal straps along the length of the pipe.

FIG. 1A shows a cross-section of a pipeline 100 which has a pipe 105, insulation 103, and weather protection 101. The relative dimensions of pipe 105, insulation 103 and weather protection 101 are illustrative. Actual pipes may have a wide range of parameters. Dimensions of note include the pipe's outer diameter, OD, inner diameter, ID, and wall thickness, $t_s$ ($t_s$=[OD−ID]/2). The insulation has a thickness, $t_i$, and the weather protection has a thickness, $t_j$.

Over time, pipe 105 can become corroded, reducing the integrity of the pipeline and increasing the risk of a catastrophic failure. Corrosion can result in localized reduction in the wall thickness of the pipe, general wall loss over large areas, or localized pits. Material loss caused by corrosion can occur on both the inner and outer surfaces of the pipe as illustrated by the exemplary interior corrosion loss 107 and exterior corrosion loss 109. Other defect types that may be formed are cracks 106, 108 (e.g. stress corrosion cracking), welding anomalies, hard spots (local increases in material hardness), and dents.

If damage becomes severe, pipe 105 may fail, for example, as a result of the pressure of the transported gas/liquid. Inspections are needed to identify locations of pipe that are likely to fail so that local replacement or repair of the pipe section can be performed preemptively avoiding pipeline failure.

Inspection can be performed from the interior or exterior of the pipe. For interior inspection, a pipe inspection gauge (PIG) is inserted into the pipe and wall thickness measurements are made using inspection techniques such as magnetic flux leakage (MFL) and ultrasound. As the PIG passes down the pipe, inspection data is recorded which can then be used to identify sections of the pipe requiring replacement or repair.

When the pipe diameter is small or the pipe was not constructed to allow for the use of a PIG, interior inspection may not be practical. The inspection may also be performed from the exterior. Conventional exterior inspection techniques require that the weather protection and insulation be removed from the pipe so that visual, ultrasonic, or another inspection method can be performed. Such an inspection typically takes a considerable amount of time to perform. Further, the insulation and weather protection typically must be replaced after the inspection adding to the expense of pipeline inspection.

SUMMARY

Detection of corrosion and other defects in piping is needed to prevent catastrophic pipeline failure. Sensors, systems and methods are provided to enable detection of such defects. These apparatus and methods are configured to characterize pipe protected by insulation and conductive weather protection. The sensors may utilize inductive and/or solid state sensing element arrays operated in a magnetic field generated in part by a drive winding of the sensor. Multiple excitation frequencies are used to generate the magnetic field and record corresponding sensing element responses. Relatively high excitation frequencies may be used to estimate the properties of the weather protection and sensor lift-off while lower frequencies may be used to detect internal and external pipe damage. Linear arrays may be moved to generate damage images of the pipe providing size and location information for defects. Two dimensional sensor arrays may be used to provide imaging without moving the sensor.

One aspect relates to a sensor for small-footprint scanning. The sensor has at least one electrical connector, an array of sensing elements, and lead segments. The at least one electrical connector connects instrumentation to the sensor. The conducting drive loop has a primary segment, a return segment, and a connecting segment. The primary segment is a first distance from the array. The return segment is located outside a surface defined by the array and primary segment and at a second distance, at least three times the first, from the primary segment. The connecting segment connects an end of the primary segment to an end of the return segment. Finally the lead segments connect the ends of the loop to the electrical connector.

In some embodiments, the array and primary segment are straight such that the surface is a planar surface.

In some embodiments, the array and primary segment are curved about a common axis such that the surface is a cylindrical surface.

In some embodiments, the return segment is also curved about the common axis and is radially inward from the primary segment with respect to the common axis.

In some embodiments, the connecting segment is normal to the surface defined by the array and primary segment.

In some embodiments, the conducting drive loop comprises a plurality of turns.

In some embodiments, the sensing elements of the array are inductive loops.

In some embodiments, the sensing elements of the array are solid-state devices.

Another aspect relates to a method of measuring material properties at a test location of a test object with such a sensor. The method comprises flexing the sensor to a shape conforming to that of the test object; calibrating the sensor away from the test location on the test object while maintaining the shape; and operating the sensor at the test location to measure the material properties.

Another aspect relates to a system for detecting damage in a hollow cylinder through an outer non-conducting layer which is further surrounded by a thin conducting layer. The system comprises a sensor, an analyzer, and a processor. The sensor has an array of sensing elements, a drive winding, and a gap therebetween. The analyzer is operably connected to the sensor and configured to drive a current in the drive winding at a plurality of measurement frequencies and to measure a response of each sensing element in the array at each measurement frequency. The processor is configured to (i) estimate at least one material property of the thin conducting layer from at least the response of the sensing elements of the array at a first measurement frequency among the plurality of measurement frequencies, (ii) estimate a spacing between the thin conducting layer and the hollow cylinder, and a wall thickness of the hollow cylinder from at least the response of the sensing elements of the array at a second measurement frequency among the plurality of measurement frequencies, where the second measurement frequency is a lower frequency than the first measurement frequency, and (iii) determine damage to the hollow cylinder based on the estimates.

In some embodiments, the processor is further configured to estimate a lift-off of the sensor from the conducting layer from at least the response of the sensing elements of the array at the first measurement frequency.

In some embodiments, the processor is further configured to identify regions of external and internal wall loss of the hollow cylinder using the estimated spacing between the thin conducting layer and the hollow cylinder and the estimated wall thickness of the hollow cylinder.

In some embodiments, the array of sensing elements is a first array of sensing elements, the sensor further comprises a second array of sensing elements with a different gap to the drive winding, the impedance analyzer is further configured to measure responses of each sensing element in the second array at a second plurality of measurement frequencies that may or may not be different than the first plurality of measurement frequencies, and the processor is configured to utilize the responses from both the first and second arrays to determine damage.

In some embodiments, the analyzer is configured to drive the drive winding at each of the plurality of measurement frequencies sequentially and measure the responses at each sensing element simultaneously using a parallel architecture.

In some embodiments, the processor is configured to use assumed properties of the thin conducting layer if the estimated material property of the thin conducting layer indicates that the thin conducing layer has a conductivity-thickness product below a threshold, and to use the estimated material property of the thin conducting layer if the estimated material property is above the threshold.

In some embodiments, the system further comprises a non-transient computer-readable storage medium operably connected to the processor, said storage medium having a precomputed database of sensor responses, and the processor is configured to generate the estimates by comparing the sensing element responses to responses stored in the precomputed database. The database stored in the non-transient computer-readable storage medium may be responses precomputed based on a planar physics-based layered media model, a numerical method, on a physics-based model that accounts for the cylindrical shape, or generated in any other suitable way.

In some embodiments, the array of sensing elements is a first array and the sensor further comprises a second array of sensing elements having the same gap to the drive winding as the first but located on an opposite side of the drive winding as compared to the first array. The responses of the first and second array may be used to correct for the effects of motion and to measure the velocity of the sensor relative to the hollow cylinder.

Yet another aspect relates to a method of operating such a system, and where the hollow cylinder is a pipe, the non-conducting layer is an insulating layer surrounding the pipe, and the thin conducting layer is a metal weather protection. The method comprises (i) calibrating the sensor, (ii) positioning the sensor on the weather protection, and (iii) operating the analyzer and processor to obtain sensing element responses at each of the plurality of measurement frequencies and to provide the estimates and determination of damage to the pipe.

In some embodiments, the processor outputs the determined damage to the pipe as an amount of internal corrosion loss and an amount of external corrosion loss at locations on the pipe.

In some embodiments the method further comprises (iv) moving the sensor along the pipe while repeatedly operating the analyzer to obtain sensing element responses; and (v) operating the processor to generate the estimates and provide an image of the pipe damage. When positioning the sensor, the array may be aligned in the circumferential direction of the pipe, and moving the sensor along the pipe comprises movement in the axial direction of the pipe. As one alternative the array may be aligned in the axial direction of the pipe, and moving the sensor along the pipe comprises movement in the circumferential direction of the pipe. The sensor may be moved at a constant velocity reducing the effect of magnetic convection on the sensing element responses. The velocity may be recorded using a mechanical or optical encoder, or may be determined using the multi-frequency inspection data.

In some embodiments, calibrating the sensor comprises positioning the sensor in a non-conductive, non-permeable environment with the same curvature as if the sensor is positioned on the metal weather protection.

Another aspect relates to a method for inspecting a complex piping feature. The method comprises (i) wrapping a pipe having insulation with weather protection, the weather protection having a conductivity-thickness product below a threshold; (ii) positioning a magnetoquasistatic sensor adjacent to the weather protection; (iii) measuring multi-frequency responses of the magnetoquasistatic sensor at the complex piping feature; and (iv) estimating damage to the pipe by comparing the multi-frequency responses to responses predicted assuming the weather protection has a predetermined conductivity-thickness product that is below the threshold.

In some embodiments the insulated pipe is wrapped with a stainless steel weather protection. The complex pipeline feature may be an elbow, T-joint, or protrusion portion of a pipeline.

In some embodiments the weather protection is a replacement weather protection, and the method further comprises identifying an existing weather protection as having a conductivity-thickness product in excess of the threshold; and removing the existing weather protection.

Yet another aspect relates to a method comprising (i) securing a sensor having a drive winding and a two-dimensional array of sensing elements to an exterior surface of a test component, the test component comprising a hollow cylindrical conductor surrounded by an insulating layer; (ii) exciting the drive winding at a plurality of measurement frequencies; (iii) measuring responses at each of the plurality of measurement frequencies on each of the plurality of sensing elements in the two-dimensional array; (iv) based on the measured responses, providing an estimate of wall loss for the hollow cylinder.

In some embodiments the sensor is secured to a bend region, T-joint, rounded protrusion or other complex feature of the test component. In some embodiments, the test component is a pipe.

In some embodiments, the test component further comprises a thin conducting layer surrounding the insulating layer and the estimate takes into account the properties of the insulating layer and the thin conducting layer.

In some embodiments, estimating at least one property of the insulating layer and the thin conducting layer is based on the measured responses and the wall loss is estimated by accounting for the insulating layer and the thin conducting layer using such estimated properties. Though, in another embodiment the estimate of wall loss accounts for the thin conducting layer by assuming all relevant properties of the thin conducting layer.

The foregoing is a non-limiting summary of the invention, which is defined by the attached claims.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 3A-L shows configurations of the sensor for the system according to some embodiments;

DETAILED DESCRIPTION

The inventors have recognized and appreciated that there is a need for exterior pipe inspection that does not require the removal or subsequent replacement of the pipe's insulation and weather protection (if present). Methods and apparatus are provided that enable inspection of the pipe for corrosion under insulation (CUI) and other pipe defects through the insulation and weather protection. Other defect types that may be detected include, for example and not limitation, stress corrosion cracking (SCC), welding anomalies, hard spots (local increases in material hardness), and dents.

The inventors have recognized and appreciated that deep penetrating magnetoquasistatic (MQS) sensor arrays may be used to detect corrosion and other defects through insulation. In some embodiments, an array of solid-state sensing elements is used. Any type or combination of types of MQS sensing elements may be used in the array. For example, magnetoresistive (MR), hall effect, or any other type of sensing element capable of responding to magnetic fields that have penetrated into or through the pipe wall may be used. Typically, sensing elements that are marketed as MR are anisotropic magnetoresistive (AMR) elements. In some embodiments, giant magnetoresistive sensor (GMR) arrays are used. (Generally the term MR is used so as to include GMR as a special case.) MR elements directly detect magnetic fields as compared to inductive elements which detect changes in magnetic fields. A discussion of MR-Arrays and GMR-Arrays is provided in U.S. Pat. No. 6,992,482 (Jan. 31, 2006) which is incorporated by reference in its entirety.

Figure 1A:
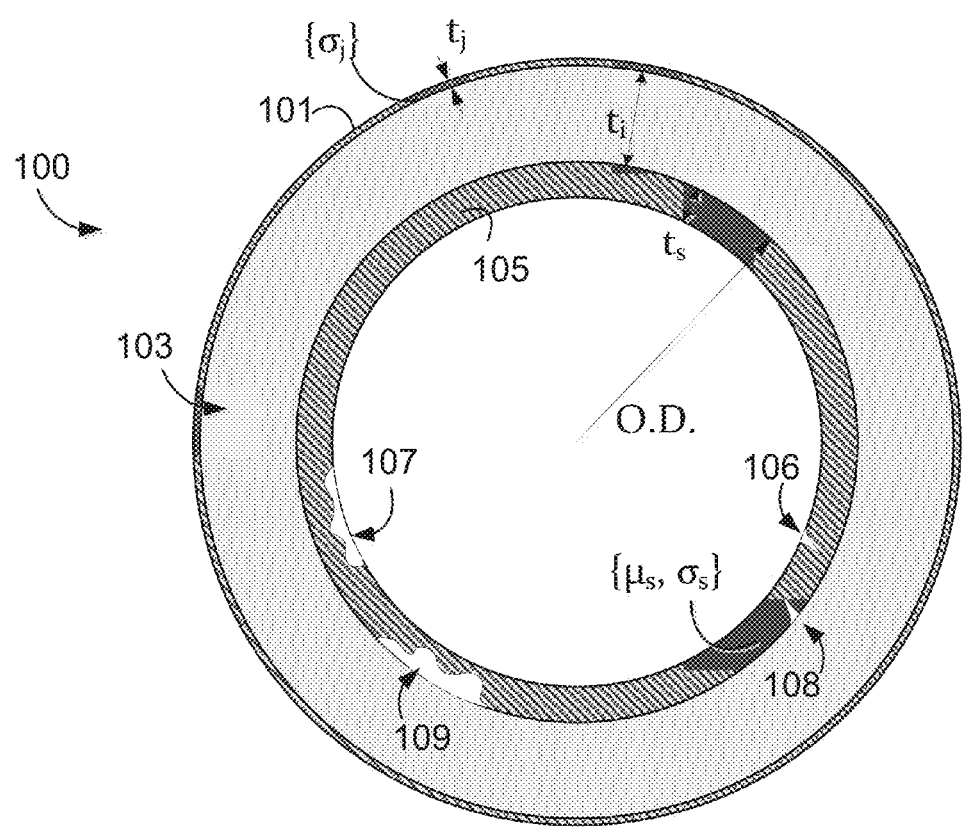
FIG. 1A shows a cross section of a pipeline.
Figure 2:
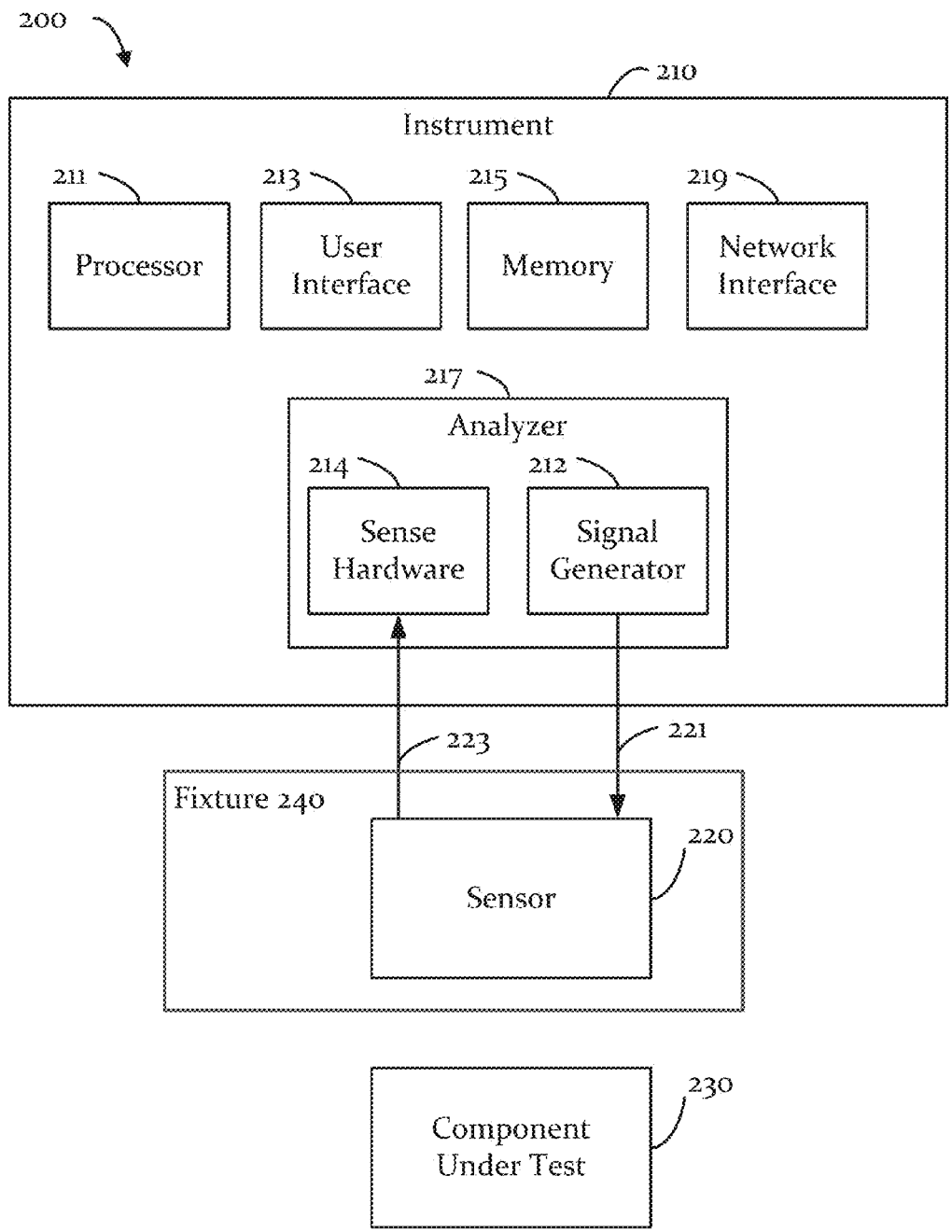
FIG. 2 shows a system with instrumentation and sensors for interrogating a component under test according to some embodiments.

Attention is now turned to FIG. 2 which shows a block diagram of a system 200 for inspecting the condition of a component under test 230. Component under test 230 may be a section of pipe such as that described above in connection with FIG. 1A. Though, component under test 230 may be any suitable test article. System 200 includes an instrument 210 and a sensor 220. Instrument 210 is configured to provide excitation signals 221 to sensor 220 and measure the resulting response signals 223 from sensor 220. Measured response signals 223 may be processed to estimate properties of interest, such as electrical properties (e.g., conductivity, permeability, permittivity), geometric properties (e.g., thickness, sensor lift-off), material condition, or any other suitable property or combination thereof (Sensor lift-off is the effective spacing between a sensing element and the component under test.)

Instrument 210 may include a processor 211, a user interface 213, memory 215, an analyzer 217, and a network interface 219. Though, in some embodiments of instrument 210 may include other combinations of components. While instrument 210 is drawn as a single block, it should be appreciated that instrument 210 may be physically realized as a single "box"; multiple, operably-connected "boxes", or in any other suitable way. For example, in some embodiments it may be desired to provide certain components of instrument 210 as proximal to sensor 220 as practical, while other components of instrument 210 may be located at greater distance from sensor 220.

Processor 211 may be configured to control instrument 210 and may be operatively connected to memory 215. Processor 211 may be any suitable processing device such as for example and not limitation, a central processing unit (CPU), digital signal processor (DSP), controller, addressable controller, general or special purpose microprocessor, microcontroller, addressable microprocessor, programmable processor, programmable controller, dedicated processor, dedicated controller, or any suitable processing device. In some embodiments, processor 211 comprises one or more processors, for example, processor 211 may have multiple cores and/or be comprised of multiple microchips.

Memory 215 may be integrated into processor 211 and/or may include "off-chip" memory that may be accessible to processor 211, for example, via a memory bus (not shown). Memory 215 may store software modules that when executed by processor 211 perform desired functions. Memory 215 may be any suitable type of non-transient computer-readable storage medium such as, for example and not limitation, RAM, a nanotechnology-based memory, one or more floppy disks, compact disks, optical disks, volatile and non-volatile memory devices, magnetic tapes, flash memories, hard disk drive, circuit configurations in Field Programmable Gate Arrays (FPGA), or other semiconductor devices, or other tangible, non-transient computer storage medium.

Instrument 210 provides excitation signals for sensor 220 and measures the response signal from sensor 220 using analyzer 217. In some embodiments, analyzer 217 is an impedance analyzer. Though, analyzer 217 may provide excitation and measure response signals in any suitable way.

Analyzer 217 may contain a signal generator 212 for providing the excitation signal to sensor 220. Signal generator 212 may provide a suitable voltage and/or current waveform for driving sensor 220. For example, signal generator 212 may provide a sinusoidal signal at one or more selected frequencies, a pulse, a ramp, wavelet, or any other suitable waveform. Where interrogation of component under test 230 is to be performed at multiple frequencies, the frequencies may be excited sequentially, simultaneously, or in any suitable way.

Sense hardware 214 of analyzer 217 may include multiple sensing channels for processing multiple sensing element responses in parallel. Though, other configurations may be used. For example, sense hardware 214 may include multiplexing hardware to facilitate serial processing of the response of multiple sensing elements. Sense hardware 214 may measure a voltage or current from on one or more sensing elements of sensor 220. In some embodiments, sensing hardware 214 represents the sensing element response as a transimpedance. That is, the ratio of a voltage measured across the terminals of a sensing element to a drive current provided by signal generator 212. Though, other measures may be used. Analysis of data sampling of portions of a waveform may be taken locally, for example, with FPGAs or other hardware and/or software.

Sensor 220 may be any suitable sensing technology or combination of sensing technologies. In some embodiments sensor 220 is a MQS sensor having a drive winding and an array of MQS sensing elements. The array may be arranged, for example, in a linear configuration or in a two-dimensional configuration. Though any suitable configuration may be used.

A fixture 240 may be used to facilitate acquiring sensor data from component 230. For example, fixture 240 may be a mechanical structure that facilitates positioning sensor 220 at desired locations relative to component 230. In some embodiments, fixture 240 is a scanning fixture easing the movement of sensor 220 along a scan path on component 230.

Memory 215 of instrument 210 may store computer-executable software modules that contain computer-executable instructions. These modules may be read for execution by processor 211. Though, this is just an illustrative embodiment and other storage locations and execution means are possible.

In some embodiments, the computer-executable software modules may include a sensor data processing module, that when executed, estimates properties of the component under test. The sensor data processing module may utilize property grids stored in memory 115. The property grids are multi-dimensional pre-computed databases that relate single or multiple frequency measurements obtained by analyzer 217 from sensor 220 to material properties to be estimated. The sensor data processing module may take the property grids and sensor data and, using grid methods, estimate material properties. (Grid methods are also discussed in U.S. Pat. No. 6,992,482.)

User interface 213 may include devices for interacting with a user. These devices may include, by way of example and not limitation, keypad, pointing device, camera, display, touchscreen, audio input and audio output.

Network interface 219 may be any suitable combination of hardware and software configured to communicate over a network. For example, network interface 219 may be implemented as a network interface driver and a network interface card (NIC). The network interface driver may be configured to receive instructions from other components of instrument 210 to perform operations with the NIC. The NIC provides a wired and/or wireless connection to the network. The NIC is configured to generate and receive signals for communication over network. In some embodiments, instrument 210 is distributed among a plurality of networked computing devices. Each computing device may have a network interface for communicating with other the other computing devices forming instrument 210.

The solid-state sensing elements may be used in combination with an inductive sensor array. For example, an inductive array and solid-state array may be used in combination with one another as a single sensor 200 as shown in FIG. 2. The drive winding 201 may be excited at multiple frequencies to produce a drive current and magnetic field. The response of the sensing elements will depend upon the magnetic field generated produced by the drive current and upon the proximity to the pipeline, the pipelines materials, and the condition the pipeline is in. The sensing element responses may be measured and recorded and the process repeated at multiple locations on the pipe. In some embodiments the array is scanned along the pipe so that these repeated measurements may be used to produce and image of the pipe, detecting and sizing defects. For example, axial or circumferential scans may be performed. Though, scanning may be performed in any suitable way. The measurements are processed to determine whether defects in the pipe are present so that appropriate action may be taken.

FIG. 3A shows an example of sensor 300 comprising a drive winding 301, an array of sensing elements 303 and a connector 302. Sensor 300 may be used in the same ways as sensor 220 in system 200 of FIG. 2. Drive winding 301 and array 303 are separated by a drive-sense gap 305. Drive-sense gap 305 is a characteristic distance between the nearest portion of drive winding 301 and array 303. Whether gap 305 is defined from center-to-center, edge-to-edge, or in another way is not critical. (In FIG. 3A gap 305 is shown as edge-to-edge, but this is merely illustrative.) Drive-sense gap 305 may be selected to limit edge effects from pipe ends and other geometry changes, straps securing weather protection, screws and other securing features, metal mesh in the insulation, overlap regions of the weather protection, and other complicated geometries such as elbows and T-joints.

Connector 302 facilitates connection of the drive winding 301 and sensing elements to appropriate instrumentation such as instrument 210 (FIG. 2). Connector 302 provides suitable electrical connections for the components of sensor 300 and facilitates signal isolation between the various elements. In some embodiments, connector multiple physical connectors are used. Multiple physical connectors may be desired, for example, to provide greater isolation of the drive signal from the sensing element returns.

In the illustrated embodiment, drive winding 301 is a "double-D" drive winding. It has two large loops that may be driven to carry current in the same direction in the adjacent winding sections of the loops. The loops may have multiple turns to increase the amount of magnetic flux coupled to the array elements. A double-D drive winding constructed for experimental validation had about 70 turns. Though, the loops may have any suitable number of turns to produce a sufficient magnetic field to, for example, provide the necessary sensitivity to defects in the pipe for a given pipe geometry. In other embodiments drive winding 301 may have only a single drive loop or more than two loops. Any suitable drive configuration may be used as certain configurations may be more desirable depending upon specific constraints of the application.

In some embodiments, analytical models that treat the drive winding as a current sheet are used to interpret sensing element measurements. In such embodiments, drive winding 301 may be wrapped with multiple turns to simulate a planar current sheet. To achieve such an effect a flattened ribbon wire with a thin insulating coating may be wrapped with tight placement where each turn is adjacent to the next approximating an evenly distributed current sheet at low frequencies.

Figure 3B:
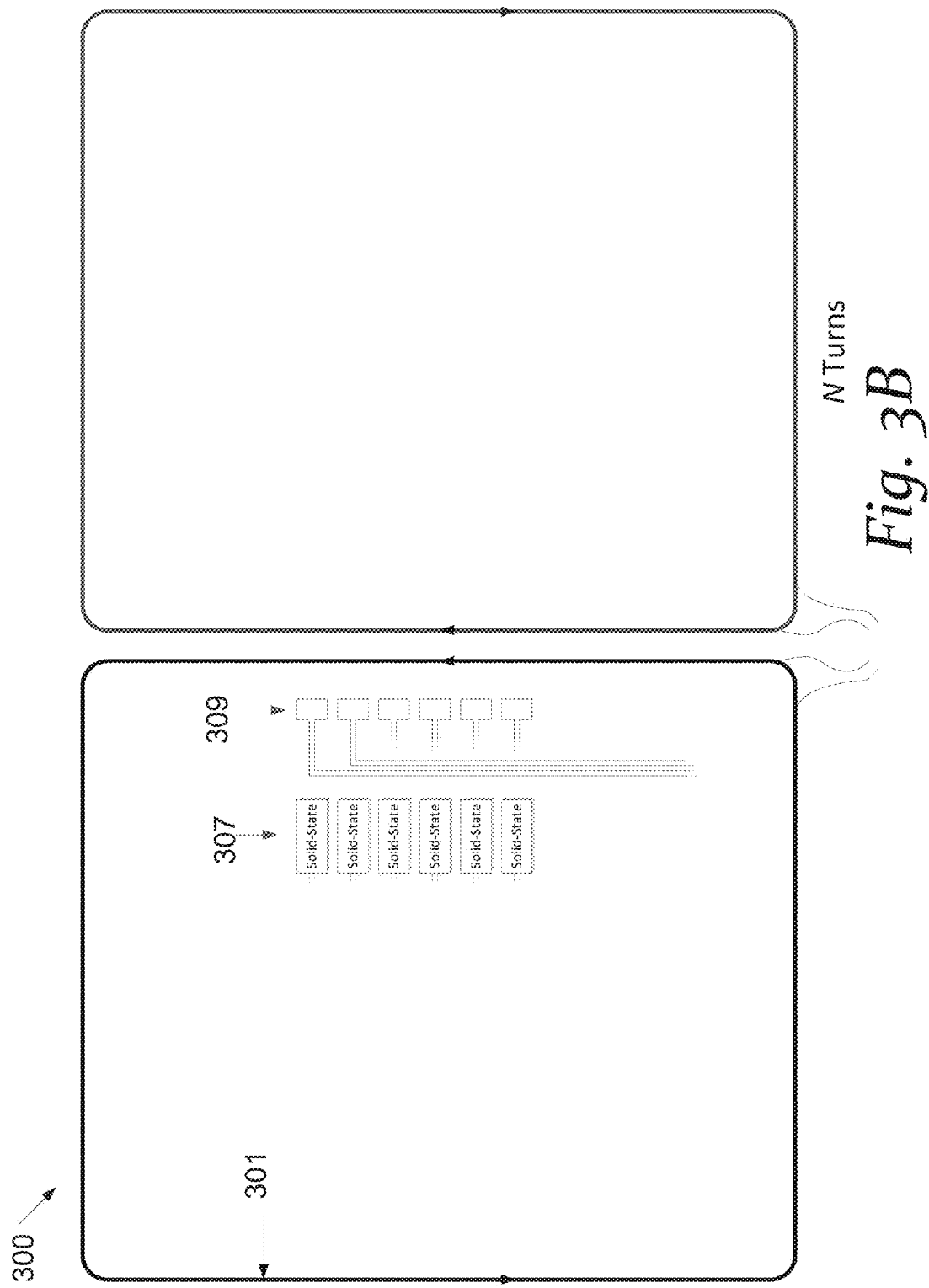

In some embodiments sensor 300 has multiple arrays of sense elements placed in a single drive loop. In this configuration each row has a different drive-sense gap, potentially increasing the independent information provided by the sense element when estimating material properties. FIG. 3B shows an embodiment of sensor 300 with a first array 307 of solid-state sensing elements and a second array 309 of inductive sensing elements. The conducting loops of the inductive sensing elements of array 309 may have one or more turns. The size of the loops and distance of the loops from the drive winding may be chosen, for example, to provide suitable sensitivity to the properties of weather protection 101 of pipeline 100 (FIG. 1A) while being insensitive to the thickness of the insulation and properties of pipe 105 itself. As shown in FIG. 3B, the solid-state elements of array 307 may be at a greater drive-sense gap than the inductive sensing elements of array 309. Generally, this will cause the solid-state elements to couple more strongly with deeper penetrating magnetic field. In some embodiments the distance is sufficient such that at suitable frequencies the magnetic field coupled to the solid-state elements is sensitive to the thickness of pipe 105.

Figure 3C:
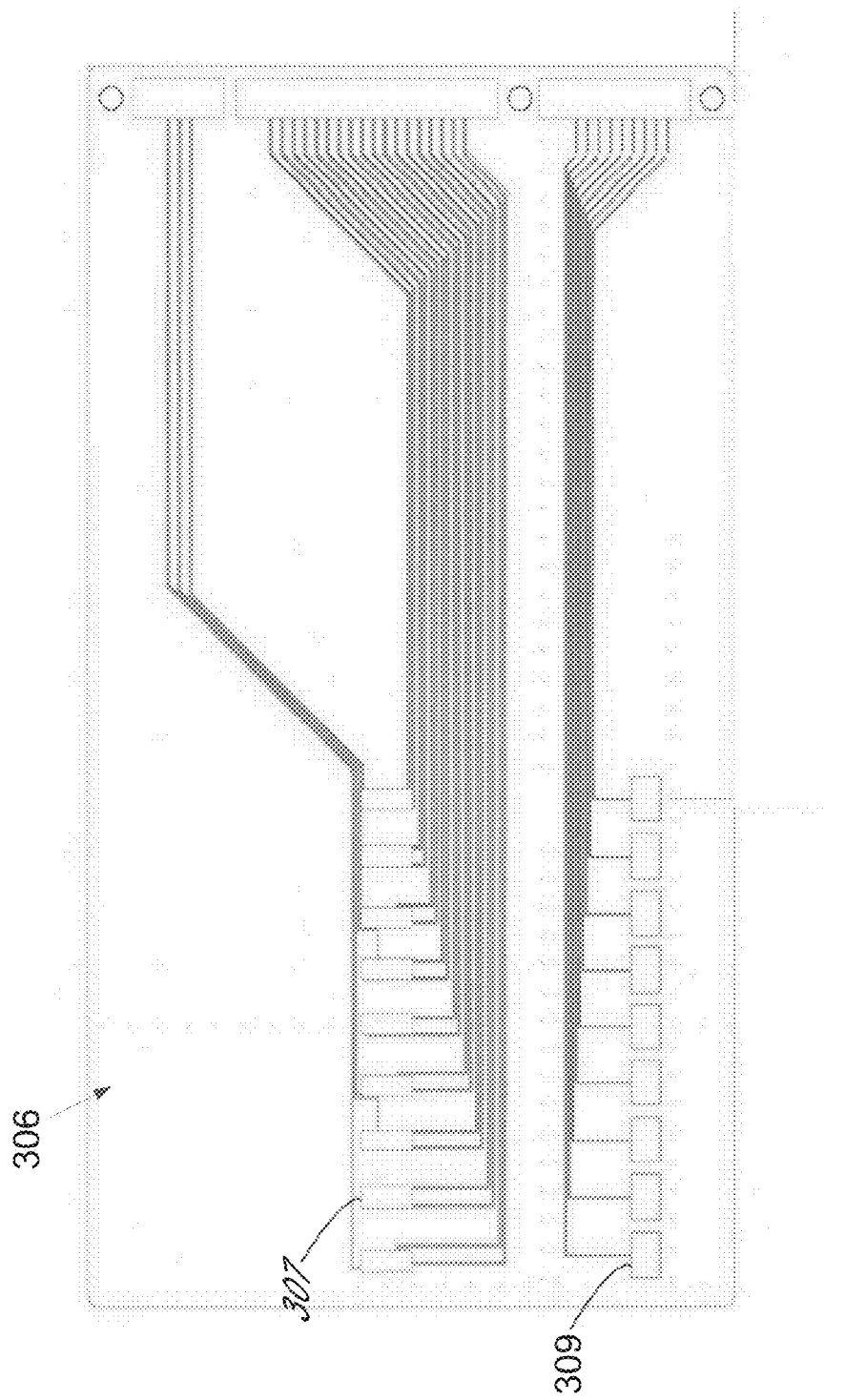

It may be desirable to provide sensor 300 such that the relative position of array 303 with respect to drive winding 301 may be readily adjusted. In such a "variable-wavelength" sensor configuration, drive winding 301 may be constructed separate from the sense elements. This capability is particularly valuable during initial configuration of an inspection as the optimal distance from the sensing elements to drive winding may not be known initially. Gap 305 may be varied to achieve different depths of sensitivity. (Increasing gap 305 will increase the depth of sensitivity.) FIG. 3C shows a substrate 306 having array 309 of inductive elements and array 307 of solid-state elements. Drive winding 301 (FIG. 3B) may be formed, for example with a separate substrate and the two substrates stacked and shifted relative to one another to achieve any desired drive-sense gap. In this example the solid-state elements and the inductive elements are formed on the same substrate, though, in some embodiments, the arrays may be formed separately to permit independent adjustment of the distance to the drive winding loops.

It is noted that the choice of 9 elements is application specific and it should be appreciated that the number and spacing of elements is not critical. The number of elements in the array may be chosen in any suitable way. For example, once array element size has been determined based on the sensitivity requirements, the elements may be configured to completely surround the pipe so as to permit scanning in the axial direction of the pipe in one scan. In another embodiment, the arrays are wide enough so that the entire sensor spans between the metal straps securing the insulation and weather jacket. This configuration may be convenient for scanning around the pipe and incrementally repositioning the sensor along the pipe after each scan. Other configurations may also be used.

FIG. 3D shows another embodiment of sensor 300 where solid-state elements may be arranged in array 307 and array 308. Arrays 307 and 308 are positioned on both side of the drive. In some embodiments the two arrays have the same drive-sense gap. Scanning in this configuration provides redundancy and to facilitates for correction of errors associated with magnetic convection. Magnetic convection may become relevant when the magnetic diffusion time is sufficiently high (i.e., the excitation frequency is sufficiently low) relative to material transport time (i.e., scan speed). Uncorrected for, convection will introduce a phase shift that is not present when taking stationary measurements. Magnetic convection may be particularly significant when measuring the thickness of thick steels a material commonly used for oil and gas pipe. The solid-sate sense element locations may be adjusted to enhance or reduce sensitivity to convection. For example, if the array elements are centered within the loop of the double-D they will be less sensitive to convection.

Figure 3E:
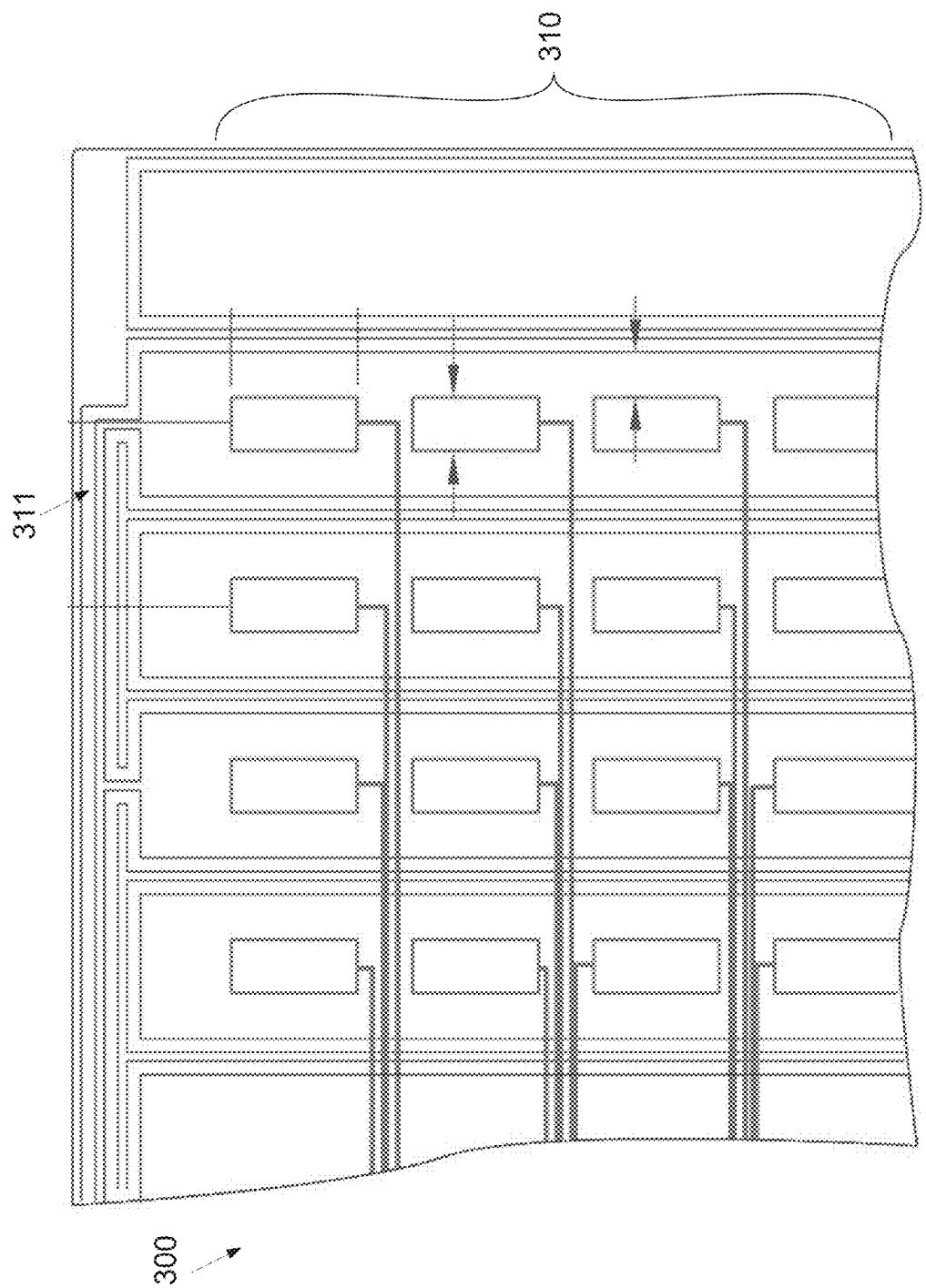

FIG. 3E shows yet another embodiment of sensor 300. Specifically, FIG. 3E shows a detail of a two-dimensional array 310 and drive winding 311. As illustrated by the figure, array 310 has sensing elements in two directions. Such a sensor may be used to image an area without moving the sensor. Though array 310 is shown as inductive loops, it should be appreciated that any suitable magnetoquasistatic sensing element may be used.

Figure 3F:
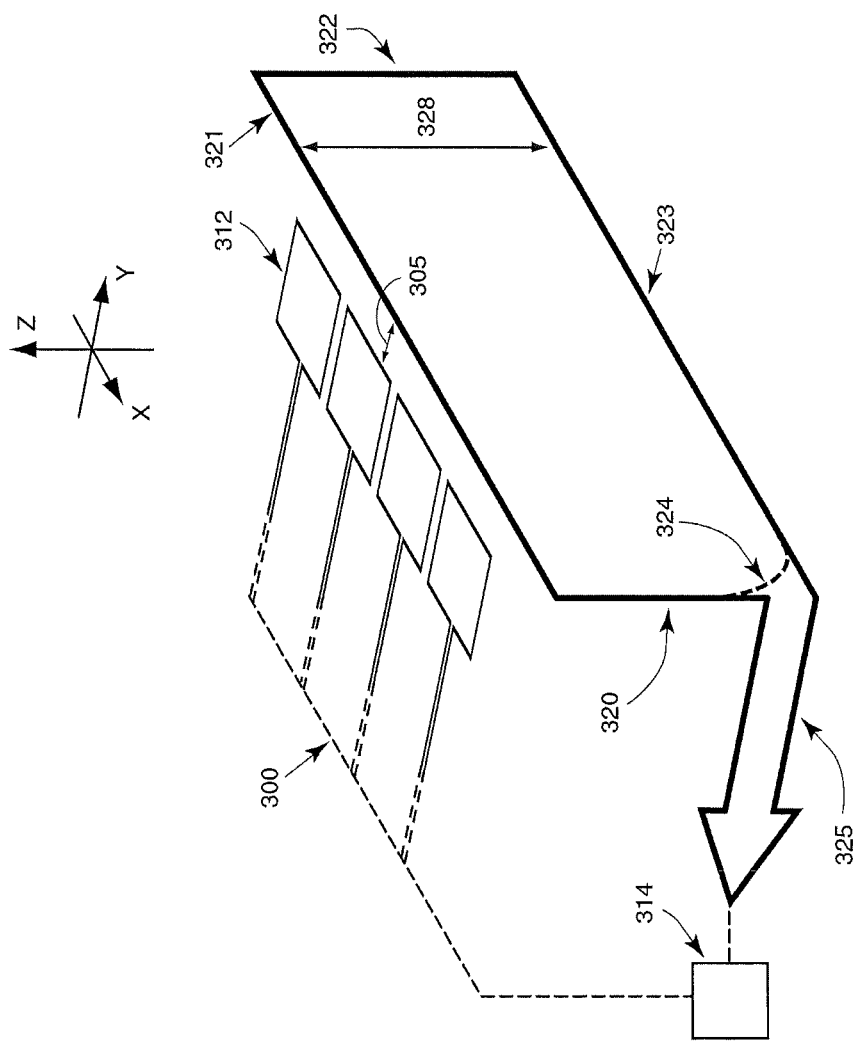

FIG. 3F shows another embodiment of sensor 300. Here drive winding 320 is a rectangular loop that is not coplanar with the sensing array 312. Drive winding 320 has a primary segment 321 nearest the array and which is used to define the drive-sense gap 305. Primary segment 321 and array 312 define a surface; in the coordinate system shown they specifically define the x-y plane. The drive winding further has a return segment 323 outside the surface defined by primary segment 321 and array 312. In some embodiments, return segment 323 is substantially parallel to primary segment 321. A connecting segment 322 connects one end of primary segment 321 to an end of return segment 323. A fourth segment 324 will connect the remaining end of either primary segment 321 or return segment 323 to lead segments 325. Drive winding 320 may have multiple turns such that each of the four segments is formed from multiple wires. Drive winding 320 may be formed with multiple turns in ways similar to those described above.

In some embodiments, primary segment 321 and return segment 324 are separated by at least three times the drive-sense gap 305. Such separation may be provided to reduce to the influence of the magnetic field produced by return segment 324 on the response of array 312.

Connecting segment 322 and fourth segment 324 are shown perpendicular to the surface defined by primary segment 321 and array 312 (i.e., in the z-direction). This configuration is merely illustrative and segments 322 and 324 may have different orientations.

Figure 3G:
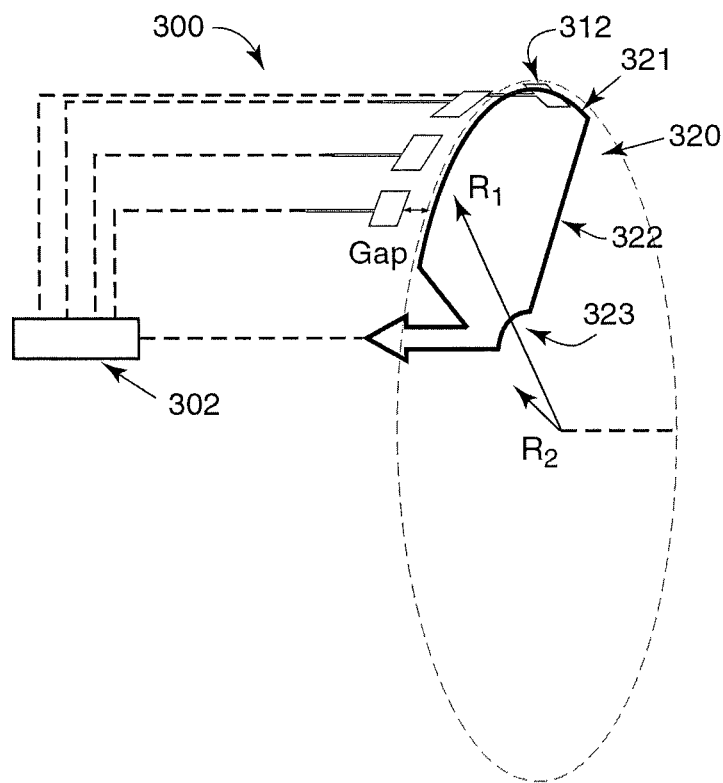
Figure 3H:
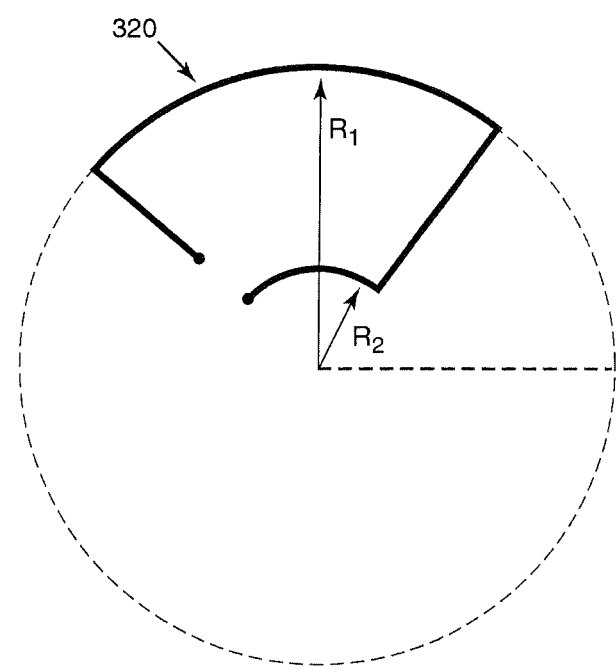
Figure 3J:
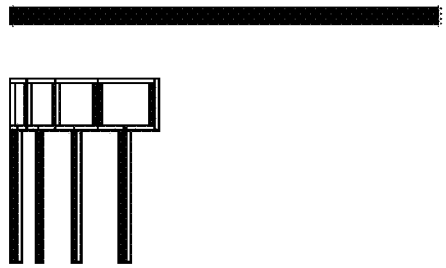
Figure 3I:
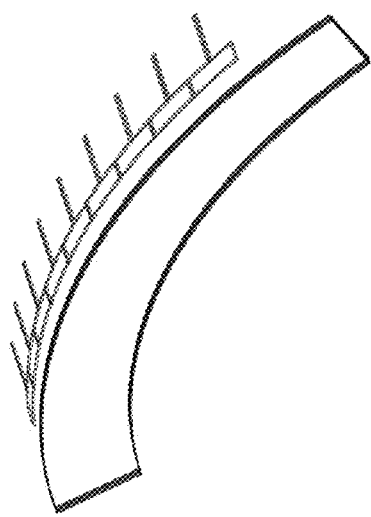
Figure 3K:
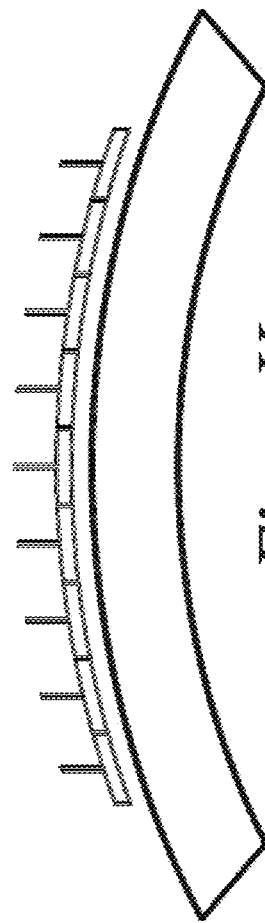

FIG. 3G shows another embodiment of sensor 300. Here the sensor is similar to that shown in FIG. 3F except the geometry is configured for a cylindrically shaped test materials. The sensing elements of array 312 follow a circular path with radius $R_1$ as does primary segment 321 of drive winding 320. Return segment 323 is shown following a radius $R_2$. Primary segment 321 and return segment 323 are joined radially by connecting segment 322. While in the illustrated embodiment, $R_2$ is shown smaller than $R_1$, this is merely illustrative, and the opposite configuration may be used. Further, such segments may be flexible such that conformance to a component under test is made possible.

Figure 3L:
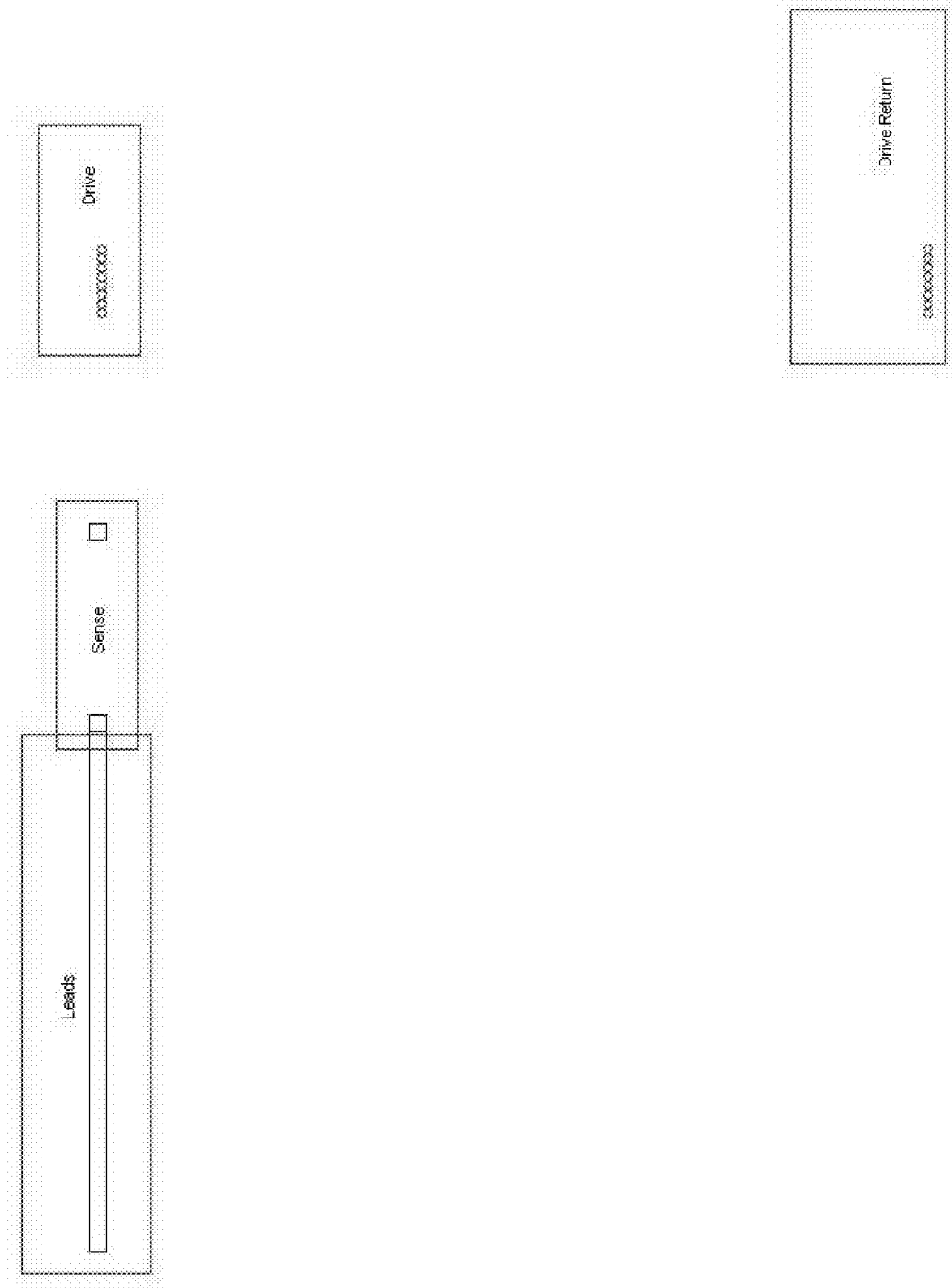

FIGS. 3H-K show drive winding 320 and array 312 from various perspectives to provide clarity in the illustrated configuration. FIG. 3L shows drive winding 320 and array 312 in cross-section and illustrates an embodiment where drive winding 320 has multiple turns.

In the embodiment of the inductive array shown in FIG. D, each element of the inductive array has one turn and is etched on the same side of a single layer of substrate. Though, it should be appreciated that the inductive elements may have multiple turns. Multiple turns may be achieved by forming one or more turns on each side of the substrate and using via connections (a hole through the substrate that electrically connects traces on either side) to connect the turns on both sides appropriately. The ends of the first and last loop may then be connected to leads that connect the sensing loop to the instrumentation for measurement. For example, two turns may be formed on one side of the sensor substrate and another two turns may be formed on the other side of the sensor substrate and connected with vias. Multiple layers of substrate can be stacked and connected with vias or with external wiring. Elements can be formed with one or more turns of insulated wires.

The sensor may be used to take multi-frequency sensor measurements. Specifically, at each frequency a response of the sensor may be measured. The measured response may be an impedance, admittance, voltage, current, or any other suitable parameter that may be used to determine the properties of the pipe of interest. For the present discussion the measured value is assumed to represent an impedance. Though, this is illustrative and chosen merely for convenience and any suitable measure may be used.

The measurements may be related to the material properties of the pipe using a suitable inverse method. In some embodiments, grid based inversion methods such as those described in U.S. Pat. Nos. 6,992,482 and 5,453,689 (and incorporated by reference in their entirety) are used. Though, any suitable inverse method may be used.

In some embodiments, the cross-section of the pipe is modeled using a multilayer model. In some instances a planar model may be sufficient, however, a cylindrical model will more accurately reflect the actual geometry of the pipe. The model may be used, for example, to define a solution space for the inverse solution method used.

In an illustrative embodiment, a multilayer model is used to generate hyperlattices uses for the grid methods. A hyperlattice is a multi-dimensional database for relating a set of known values to a set of unknown values using the grid methods. (A grid is such a database which relates 2 known parameters to 2 unknown parameters.) The model may be configured to take treat certain parameters as constants while other parameters are treated as variables to be estimated from the sensor measurements.

Returning to FIG. 1A, the following parameters are defined for a cylindrical model:
pipe outer diameter, O.D.,
pipe wall thickness, $t_s$,
pipe conductivity, $\sigma_s$,
pipe permeability, $\mu_s$,
insulator thickness, $t_i$,
insulator conductivity, $\sigma_i$,
insulator permeability, $\mu_i$,
weather jacket thickness, $t_j$,
weather jacket conductivity, $\sigma_j$, and
weather jacket permeability, $\mu_j$.

Additionally, because the sensor is assumed to be some small distance from the weather jacket, the sensor lift-off, h, must also be defined. Of course, alternative definitions of the parameters are possible (e.g., pipe inner diameter, insulation O.D., weather jacket O.D.) and any suitable set may be used. In some embodiments, certain parameters may be treated as frequency dependent. For example, the permeability of steel pipe may be dependent on frequency at the frequencies used for inspection. In some embodiments, parameters may have multiple components. For example, permeability can be modeled as having an in-phase component and an out-of-phase component.

Figure 5A:
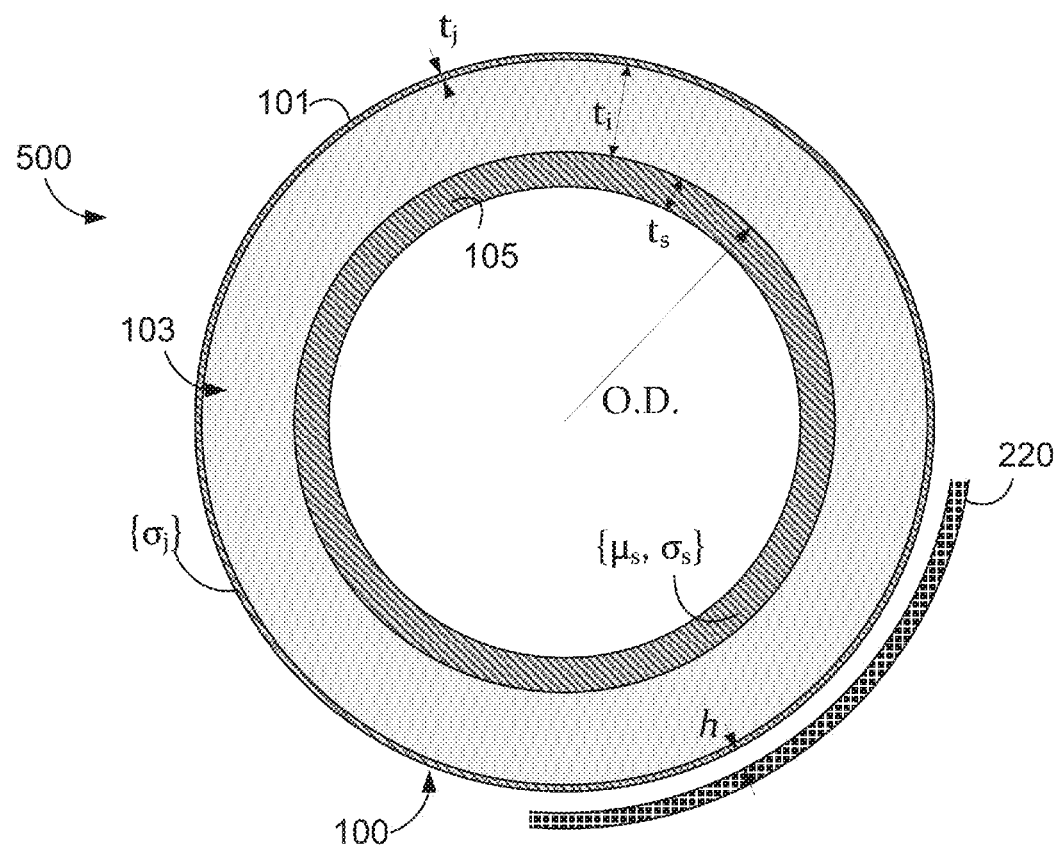
FIG. 5A is a model of a sensor and insulated hollow cylinder with weather protection that may be simulated to predict the sensor response.
Figure 5B:
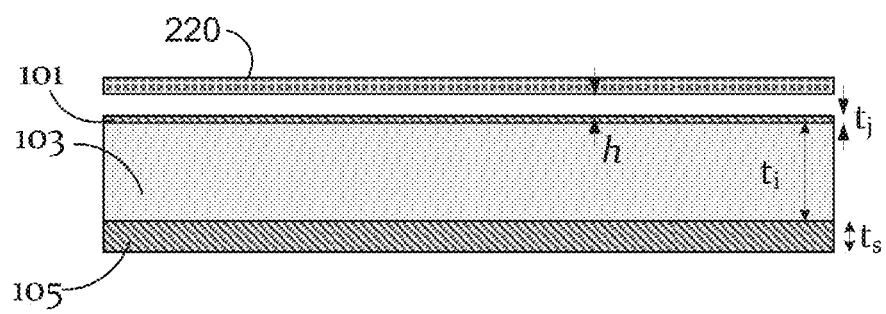
FIG. 5B is a simplified model of the sensor and insulated hollow cylinder with weather protection that may be simulated to predict the sensor response.

A planar model is shown in FIG. 5B. The parameters are the same except an O.D. is not included as by virtue of the choice of a planar model it has essentially been assumed to be infinite.

The response of one or more sensors at one or more frequencies can be used to determine the value of these parameters. In practice, some of the parameters will be assigned assumed values and some will be treated an unknown and estimated using the response of the sensors. The number of unknowns that may be simultaneously determined will depend on the specific sensor and instrumentation capabilities. For the present illustration, a 6 unknown problem is posed and demonstrated in accordance with the hardware available for testing. All other parameters have been assigned assumed values. Use of a greater or smaller number of unknowns may be appropriate depending upon the nature of the material being inspected and the instrumentation capabilities at hand.

A steel specimen having a 6⅝ inch O.D., a 0.28 inch wall thickness (nominal) 2.0 inch thick neoprene insulation (nominal), and 0.02 inch aluminum weather jacket (nominal) was studied. Based on the materials, certain parameters were given assumed values, reducing the number of parameters that needed to be estimated from measurements. A planar model was used. The parameters were defined as follows:
pipe wall thickness, $t_s$ . . . UNKNOWN
pipe conductivity, $\sigma_S$ . . . known
pipe permeability, $\mu_s$, . . . UNKNOWN—FREQUENCY DEPENDENT
insulator thickness, $t_i$ . . . UNKNOWN
insulator conductivity, $\sigma_i$ . . . 0
insulator permeability, $\mu_i$ . . . $\mu_o$
weather jacket thickness, $t_j$, . . . UNKNOWN
weather jacket conductivity, $t_j$, . . . UNKNOWN
weather jacket permeability, $\mu_j$ . . . $\mu_o$
lift-off, h, . . . UNKNOWN The pipe conductivity was chosen as a constant based on the nominal steel properties. The conductivity could be measured using, for example, a four point probe.

Thus the sensor measurements were used to estimate 6 unknowns: (1) the sensor liftoff, which represents the effective distance of the sensor from the weather jacket; (2) the thickness of the weather jacket; (3) the conductivity of the weather jacket; (4) the thickness of the insulation; and the (5) wall thickness and (6) permeability of the steel pipe. Only the permeability of the steel pipe is treated as frequency dependent.

In order to solve for all unknowns, multi-frequency measurements are taken on the inductive windings and the MR sensing elements. Typical excitation frequencies are between 30 Hz and 10 kHz. Though, any suitable frequencies may be used for measurement.

The properties of the steel pipe and the weather jacket can be decoupled by using measurements from the inductive elements which may be configured so as to be insensitive to the properties of the steel pipe. This insensitivity may result from configuring the inductive array elements to have a low penetration depth. Accordingly, the sensor lift-off and the conductivity and thickness of the weather jacket may be determined independent of the insulation thickness and pipe properties.

Using relatively high frequencies where the magnetic field does not significantly penetrate through the steel pipe, the thickness of the insulation is estimated from the MR sensors. The properties of the weather jacket and the liftoff are assumed in this estimation based on the values obtained from the inductive elements.

At lower frequencies which penetrate through the steel pipe the thickness of the steel and the permeability of the steel may be determined. The properties of the weather jacket and insulation as well as the liftoff are assumed based on the determination from the inductive sense element measurements and the high-frequency MR measurements. Thus, for each low frequency MR interrogation there are only two unknowns to be solved for: the thickness and permeability of the steel. The accuracy of the permeability measurement may be biased by the choice of conductivity for the steel which may not be entirely accurate for all locations of the pipe. The permeability can be used to help qualify, for example, the extent of damage or stress variations. The thickness of the steel will reveal information about loss of wall thickness due to corrosion. Also, the thickness of the insulation will appear to increase when the steel has corroded on the outside surface. Corrosion from the inside surface will result in reduced values of $t_s$. Other defects, including but not limited to stress corrosion cracking (SCC), may be estimated as either changes in wall thickness and/or changes in permeability.

Thus, by identifying unexpectedly large insulation thickness estimates or unexpectedly small steel thickness estimates, locations of exterior corrosion and interior corrosion can be identified, respectively.

At locations where the pipe has had wall thickness reduction, appropriate maintenance action may be taken. For example, the insulation may be removed and additional testing may be performed to verify the reduced wall thickness; the pipe may be repaired or replaced; or the location may be simply noted for future monitoring.

Figure 4:
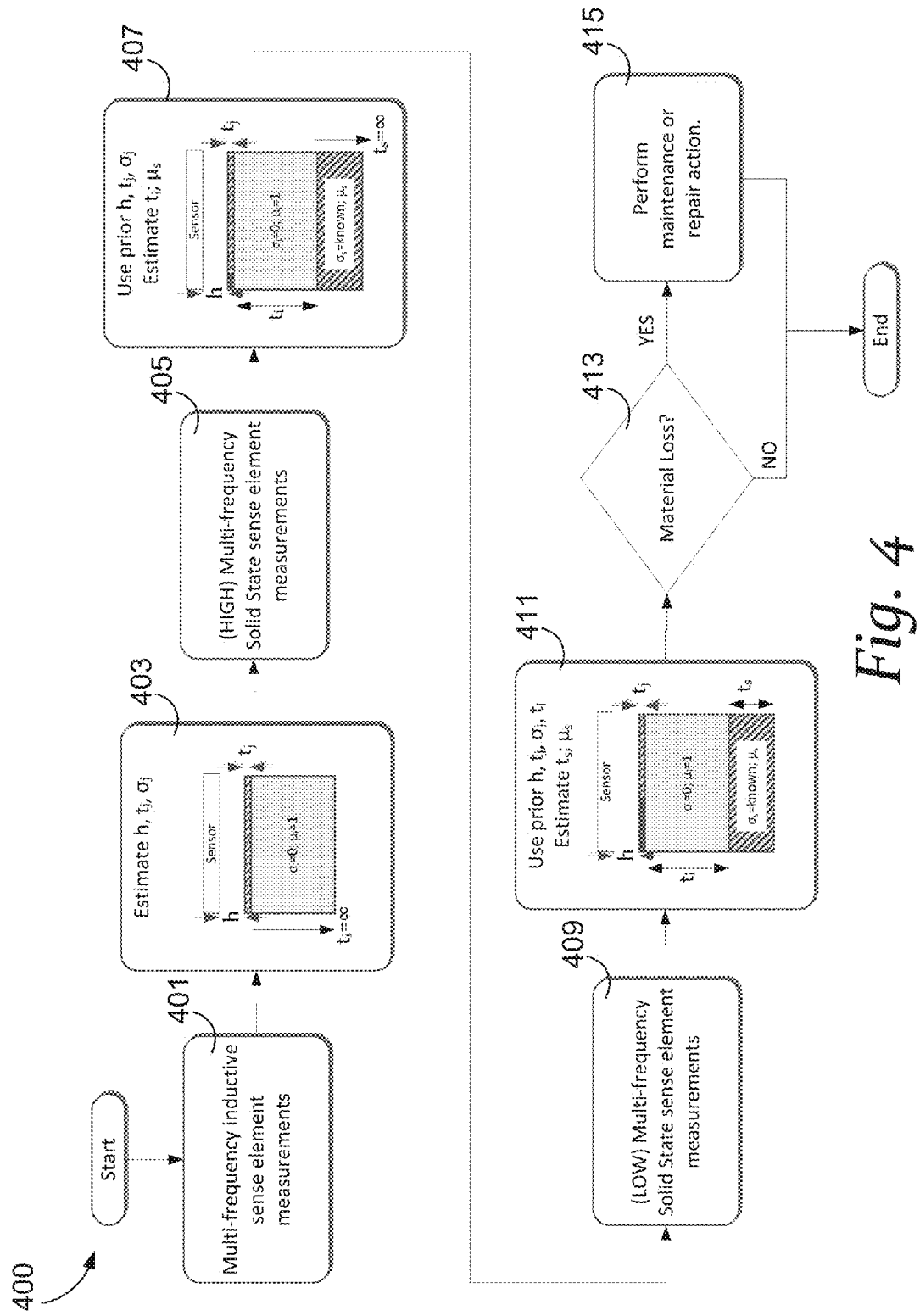
FIG. 4 is a flow diagram of a method for determining material loss and controlling performance of maintenance or repair actions on an insulated pipe with weather protection.

Method 400 shown in FIG. 4 is a method for determining material loss and controlling performance of maintenance or repair actions on an insulated pipe with weather protection. Though, method 400 may be performed for any hollow cylindrical component, regardless of the component's intended or actual use. Method 400 may be performed using system 200 show in FIG. 2, though, any suitable instrumentation and sensors may be used.

At step 401, inductive sense element measurements are performed using a sensor located on the exterior of the pipeline as show as system 500 in FIG. 5A. Specifically, FIG. 5A shows a pipeline 100 having a pipe 105, insulating layer 103, and a weather protection 101. The inductive sense element measurements may be performed at one or more frequencies such that the lift-off and weather protection properties may be estimated as necessary. Such measurements may be performed in ways described herein or in any suitable way.

At step 403, the lift-off of the sensor (h in FIG. 5A), the thickness of the weather protection ($t_j$), and/or the conductivity of the weather protection ($\sigma_j$) are estimated using the inductive sense element measurements. The measurements may be used to estimate these properties in any suitable way. For example, the response of the sensor may be pre-computed using a physics-based model and the responses stored in a database. The physics based model may account for the cylindrical shape of the pipeline or may approximate the pipeline as planar. In some embodiments the system 500 is modeled using a numerical method such as the finite element method (FEM) or any another suitable numerical method.

The measured inductive sense element responses may be related to pre-computed responses stored in the database using grid methods. Such grid methods may then provide estimates of the desired parameters. Other methods may be used to estimate the parameters. For example, any suitable form of an iterative estimation approach may be used.

In some embodiments, one or more of the lift-off, weather protection conductivity, and weather protection thickness may be assumed. For example, the thickness of the weather protection layer may be assumed and only the lift-off of the sensor and the conductivity of the weather protection layer estimated at step 403. Though this example is merely illustrative and any suitable combination of these parameters may be estimated at step 403.

At step 405, solid-state sensor measurements are taken. These measurements are taken at relatively high frequencies compared to the solid-state measurements taken at step 409 (described below). The frequencies may be selected such that the sensor is insensitive to the total pipe wall thickness. This condition enables the pipe wall thickness to be approximated as infinite simplifying analysis momentarily. In some embodiments the frequencies used at step 405 and step 409 will be lower than the excitation frequencies used at step 401.

At step 407, using the prior estimated or assumed lift-off and weather protection conductivity and thickness as well as the measurements from the solid-state sensing elements, the thickness of the insulating layer is estimated. The permeability and conductivity of the pipe may also be estimated. For example, in some embodiments the conductivity of the pipe is assumed (e.g., based on prior measurements) and the permeability of the pipe is also estimated. Because the permeability and conductivity of the pipe affect the sensor response in similar ways any errors in the assumed conductivity of the pipe may be accounted for in the permeability estimate while still achieving a accurate estimate of the insulation thickness. Step 407 assumes that the conductive sense elements and solid-state sense elements are integrated into the same sensor such that the lift-off in both configurations will be substantially identical. If separate sensors are used it may be necessary to estimate the lift-off for both configurations. The estimation may be performed in ways similar to those described in connection with step 403 or in any suitable way. FIG. 400 shows a potential model that may be used of the piping system at step 407.

Note that the insulation thickness as used here is not necessarily the true insulation thickness. Rather it would be more accurate to refer to the thickness being estimated as the distance between the outer surface of the pipe and the inner surface of the weather protection layer. Generally these distances should be substantially identical, however, material loss to the exterior of the pipe will effectively increase the estimated value. Because the thickness of the insulation may be well known this difference may be attributed to material loss in the pipe as described later in connection with steps 413-415.

At step 409, relatively low frequency measurements are taken using the solid-state sensing elements of the sensor. The frequencies may be selected such that the sensor response is dependent upon the wall thickness of the pipe. It is assumed here that the same solid-state sensor array is used at both steps 405 and 409. In some embodiments a sensor may be configured to use two different arrays of solid state elements with different drive-sense gaps such that the field penetration necessary to measure the pipe wall thickness can be achieved without necessarily using lower frequencies than those used at step 405.

At step 411, the permeability and thickness of the pipe are estimated using (i) the lift-off and the weather protection conductivity and thickness estimated/selected at step 403; (ii) the insulation thickness estimated at step 407; and (iii) the sense element measurements performed with the solid-state sensors at step 409. Note that the permeability estimate made at step 407 of the pipe is not assumed here. Rather, it is re-estimated with the thickness of the pipe.

At step 413, a determination is made as to whether material loss in the pipe has occurred. Material loss may occur either internally or externally to the pipe. In some embodiments, internal material loss is differentiated from external material loss. Whether interior or exterior wall loss has occurred in the pipe may be based on the measurements of wall thickness and insulation thickness. The nominal wall thickness and nominal insulation thickness may be used with these measurements to identify whether the type of wall loss (if any) that has occurred. For example, one algorithm for determining whether exterior wall loss has occurred is to simply compare the nominal insulation thickness with the measured insulation thickness and conclude wall loss has occurred if the latter is greater than the former. Another algorithm may further determine there is exterior wall loss if the measured insulation thickness is larger than the nominal insulation thickness and the wall thickness is less than the nominal wall thickness of the pipe by at least the same amount. Though, the identification of wall loss in the pipe may be performed in any suitable way. The results of the determination at step 413 may be output to a human readable output device or recorded or transmitted in any suitable way.

If it is determined that material loss has occurred at step 413, maintenance or repair actions may be performed. For example, the pipe may be replaced or patched at the location where the material loss has occurred. After repair or maintenance of the pipe at step 415, or the determination at step 413 that material loss has not occurred, method 400 terminates.

It should be appreciated that the steps of method 400 and the order of these steps are merely illustrative. The order of steps may be modified and based on the needs of the specific application and capabilities of the instrumentation and sensing apparatus. For example, all measurement steps (401, 405, 409) may be performed before any of the estimation steps are performed (403, 406, and 411). As another example, in some embodiments, all measurement results are processed simultaneously to provide simultaneous estimates of the unknown parameters.

Returning briefly to system 500 shown in FIG. 5A. System 500 includes a sensor 220 and a pipeline 100. System 500 may be used as a model of the sensor pipeline configuration for predicting the responses of sensor 220. In system 500, The sensor 220 is modeled as being separated from the pipeline (specifically the weather protection) by a lift-off, h. The pipe may be modeled as having an O.D., a wall thickness, $t_s$, a known conductivity and an unknown permeability. The conductivity may be estimated experimentally or using literature values. The insulating layer surrounding the pipe may be modeled as having a thickness $t_i$, a permeability of free space, and zero conductivity. The weather protection layer may be modeled as a conductive layer having a thickness $t_j$ and the permeability of free space. In embodiments where the conductivity-thickness product of the weather protection is sufficiently low (e.g., below a set threshold) the weather protection may be ignored or modeled using assumed values. The weather protection may be ignored in typical configurations where stainless steel is used as the weather protection. (Stainless steel has a substantially lower conductivity than aluminum, a commonly used weather protection material.)

While sensor 220 is shown wrapping around approximately one quarter of the circumference of the pipeline, this is merely illustrative. In some embodiments, sensor 220 may wrap completely around pipeline 100 or enable complete imaging of the pipe circumference in 2, 3, 4 or more placements.

FIG. 5B shows system 510, an alternative representation of the sensor/pipeline system using plainer coordinates. Here the outer diameter of the pipe is assumed to essentially be infinity. All other parameters are substantially analogous to those shown in FIG. 5A.

Figure 6:
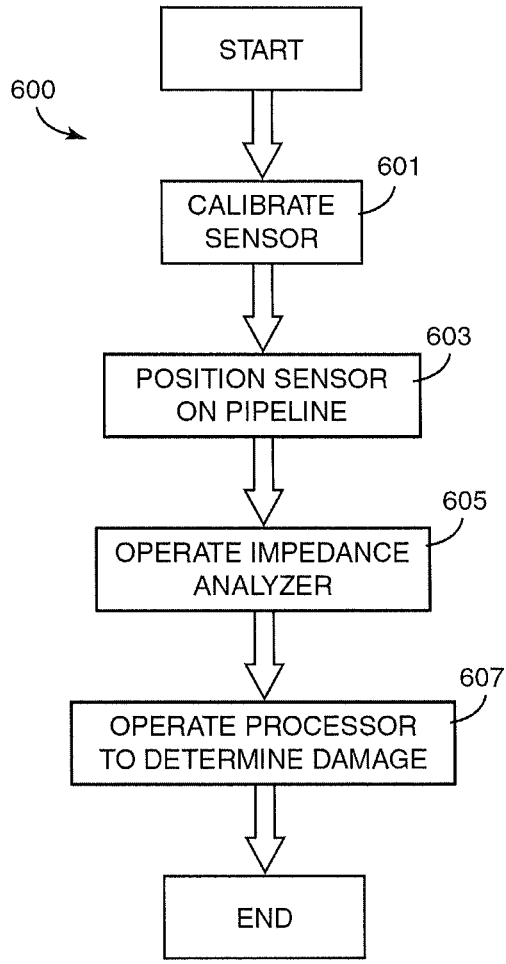
FIG. 6 is a flow diagram of a method for determining damage to an insulated pipe having weather protection.

FIG. 6 shows method 600 for determining damage to an insulated pipe having weather protection. Method 600 may be performed in the system 200 shown in FIG. 2 where component under test 230 is the pipeline. Though, any suitable system may be used.

At step 601, the sensor is calibrated. The sensor may be calibrated in air or using a reference material. In some embodiments, the sensor is held with the same geometric shape it will assume when performing interrogation of the pipeline (i.e., having the same shape taken at step 603). Air may be simulated using non-conducting, non-permeable materials such as plastics, ceramics or other such materials that do not affect magnetoquasistatic fields.

At step 603, the sensor is positioned on the pipeline's exterior. The pipeline is assumed to have a pipe surrounded by a non-conducting insulating layer which is further surrounded by a thin conducting layer.

At step 605, an analyzer is operated to drive the sensor and interrogate the sensing elements to determine responses from each element at multiple frequencies. In some embodiments the analyzer is an impedance analyzer. Though the sensor response may be measured in any suitable way.

At step 607, a processor is operated to estimate parameters of the pipe based on the multi-frequency measurements of the sensor performed at step 605. Based on these estimated parameters, it is determined at step 607 where damage has occurred to the pipeline. In some embodiments, the processor outputs the determined damage to the pipe as an amount of internal corrosion loss and an amount of external corrosion loss at locations on the pipe.

In some embodiments of method 600 the sensor is moved along the pipe while repeatedly operating the analyzer to obtain sensing element responses. The movement may be performed as a scan or by tiling. The measured responses may be processed to generate the estimates and provide an image of the pipe damage.

When tiling (also called "leap-frogging") a two dimensional array may be used to accelerate the rate of imaging of the pipe using a tiling procedure.

When scanning, the sensor may be placed on the pipe such that the array is aligned in the circumferential direction of the pipe and moving the sensor along the pipe comprises movement in the axial direction of the pipe. In another scanning embodiment, the sensor is placed on the pipe such that the array is aligned in the axial direction of the pipe and moving the sensor along the pipe comprises movement in the circumferential direction of the pipe.

When scanning the sensor during measurement magnetic convection may affect the response of the sensor. Various techniques may be used to account for the convection effects. The sensor may be moved at a constant velocity, reducing the effect of magnetic convection on the sensing element responses. The velocity information of the sensor may be recorded during the movement and the estimates provided at step 605 may utilize the velocity information to correct for magnetic convection.

Figure 1B:
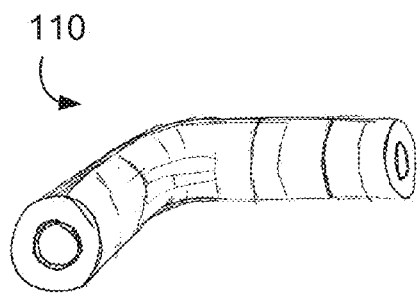
FIG. 1B-C show illustrative complex pipeline features.
Figure 1C:
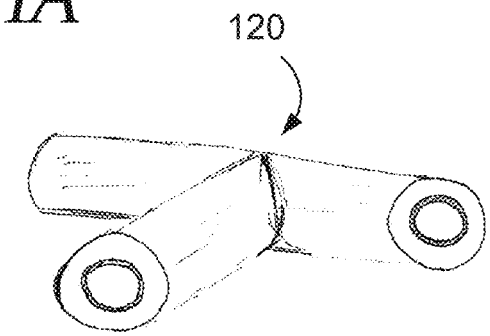
Figure 7:
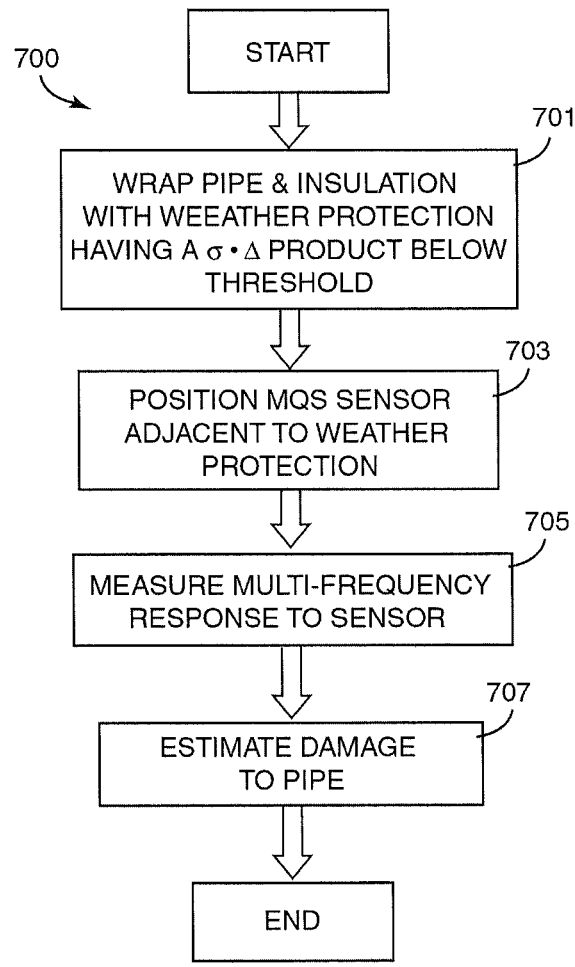
FIG. 7 is a flow diagram of a method for inspecting a complex piping feature such as pipeline elbow, T-joint, a rounded protrusion, bend, or another complex feature.

Method 700 shown in FIG. 7 is a method for inspecting a complex piping feature such as pipeline elbow 110 shown in FIG. 1B, T joint 120 shown in FIG. 1C, a rounded protrusion, bend, or another complex feature.

At step 701 weather protection having a conductivity-thickness product below a threshold is wrapped about a pipe having insulation. The conductivity-thickness product threshold may be selected such that the sensor configuration to be used for inspecting the pipe through the insulation and weather protection can image the pipe with sufficient accuracy when the weather protection is ignored or its properties are assumed without measurement. In some embodiments the insulated pipe is wrapped with stainless steel with a typical weather protection thickness such as 0.020 in. (0.5 mm). In some embodiments the weather protection is a replacement weather protection that replaces an existing weather protection that has a conductivity-thickness product that is above the threshold. For example, stainless steel weather protection may replace aluminum weather protection of nominally the same thickness.

At step 703 a magnetoquasistatic sensor is placed adjacent to the weather protection. The sensor may be a two-dimensional solid state array such as that described in connection with FIG. 3E, though, any suitable sensor may be used.

At step 705 multi-frequency responses of the magnetoquasistatic sensor are measured at the complex piping feature.

At step 707 damage to the pipe is estimated. Pipe damage may be estimate by comparing the multi-frequency responses to responses predicted assuming the weather protection has a predetermined conductivity-thickness product that is below the threshold. For example, the conductivity-thickness product may be assumed to be zero (i.e., the weather jacket is completely ignored). In some embodiments the damage to the pipe is output as an amount of internal corrosion loss and an amount of external corrosion loss at locations on the pipe. The output may be provided in any suitable format, such as on a display or on another form of human readable output. Method 700 ends after step 707.

For simplicity in the discussion above the permeability of the weather protection was assumed to be that of free space. If the weather protection is permeable (i.e., has a relative permeability greater than 1) the conductivity-permeability-thickness product may be used as the relevant metric.

Figure 8:
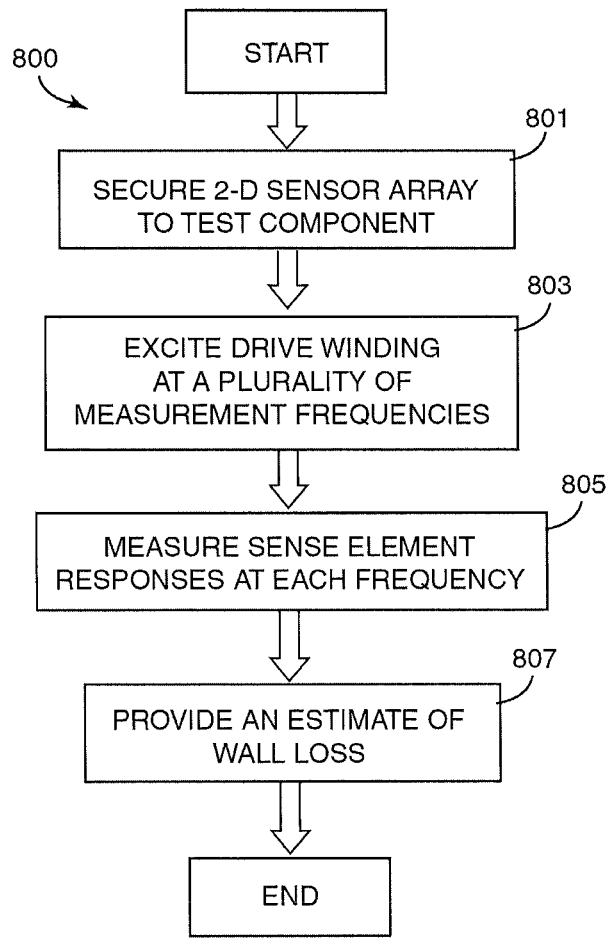
FIG. 8 is a flow diagram of a method for estimating wall loss of an insulated hollow cylinder with weather protection.

Attention is now turned to method 800 show in FIG. 8.

At step 801, a sensor having a drive winding and a two-dimensional array of sensing elements is secured to an exterior surface of a test component, the test component comprising a hollow cylindrical conductor surrounded by an insulating layer. In some embodiments the test component is a complex feature such as an elbow, T-joint, a rounded protrusion, bend, or another complex feature. In some embodiments the test component is a complex feature of a pipeline.

At step 803, the drive winding of the sensor is excited at a plurality of measurement frequencies.

At step 805, responses at each of the plurality of measurement frequencies are measured on each of the plurality of sensing elements in the two-dimensional array.

At step 807, based on the measured responses, estimates of wall loss for the hollow cylinder are provided.

In some embodiments of method 800 the test component further comprises a thin conducting layer surrounding the insulating layer and the estimate takes into account the properties of the insulating layer and the thin conducting layer. At least one property of the insulating layer and the thin conducting layer may be estimated based on the measured responses. Further the estimate of wall loss may account for the insulating layer and the thin conducting layer using such estimated properties.

MR sense element circuitry is now discussed to illustrate various configurations where MR elements are used in the sensor array. MR sense elements have many features that can be taken advantage of to provide more accurate field measurements. Selecting the MR sense element chip that has the most desirable characteristics given the application is necessary. By operating the MR element at a low-power, thermal drift can be minimized. By operating the MR element in a low magnitude field, nonlinearities intrinsic to MR elements can be minimized. MR chips have internal set-reset straps which allow for repolarization of the permalloy. Using the straps after a certain number of measurements allows for maximization of sensitivity and linearity. The internal offset straps may be used to (i) provide dynamic air recalibration to compensate for all types of drift including thermal drift; (ii) offset the Earth's magnetic field to increase MR elements dynamic range and reduce sensitivity to orientation changes; and (iii) in higher power applications, to operate as bucking coils which cancel the nominal field present during an air measurement or a measurement on a representative material, increasing the MR element's dynamic range.

Using the internal offset straps can cause problems at higher field strengths due to the thermal effects on the sensor die. In this case an external winding can be used as well to achieve the same effects as listed above.

Since the MR element directly detects magnetic fields and not changes in magnetic fields like inductive elements, bias fields can also be used advantageously. Bias fields can be used to relocate the MR element's operational point on the B-H curve with a number of effects. For example, bias fields can be varied to detect changes in impedance due to dispersive properties of a material. Also, high power bias fields can be used to saturate a material, therefore raising the frequency necessary to achieve sensitivity through the material.

Attention is now turned to various details related to imaging. With a large 2-D array, and even with a 1-D array, it is possible to build an image with stationary measurements, leapfrogging from location to location. At very low frequencies avoiding movement of the sensor avoids the convective effects. When the magnetic diffusion time is sufficiently high (the excitation frequency is sufficiently low) relative to material transport time (scan speed), there is a phase error associated with moving while taking a measurement. This is especially significant when measuring the thickness of thick steels. There are multiple approaches to dealing with this effect: (i) as mentioned earlier, building an image using stationary measurements and leapfrogging avoids this effect; (ii) by modeling the effect and then monitoring the speed using an encoder it can be accounted for; (iii) instead of using an encoder, multiple frequencies and multiple sensor rows with different drive-sense gaps can be used to estimate the sensor's speed in real-time; (iv) placing an MR element intelligently within the single-D or multiple-D drive the effect can be systematically reduced; (v) by scanning at a constant speed the phase error can be accounted for as a constant offset instead of a time-varying error.

Finally, the convective effect can be used advantageously. By using multiple frequencies and multiple sensors and/or multiple drives with different drive-sense gaps, the speed of the sensor can be estimated in real-time.

A discussion is now made of using high-permeability materials, such as mu-metals or ferrites, behind the sensor to force a higher percentage of the field created by the drive winding into the material under test. This can increase the sensor response due to material changes drastically. In addition to increasing signal levels, the mu-metal/ferrite acts a shield to external noise. Furthermore mu-metal/ferrite can be used as a backing in a non-planar form (for example curving around the edges of the sensor) in order to shape the field. This can be used to reduce sensitivity to unwanted geometries such as plate or pipe edge effects.

In order to be used effectively, the mu-metal/ferrite must be accurately modeled. The properties of the mu-metal/ferrite are most effectively determined by using the sensor for which it will serve as the backing. The sensor may be calibrated in air without the mu-metal/ferrite backing. Then, with this calibration, a multi-frequency measurement is made after the mu-metal/ferrite has been mounted. This measurement is used to determine the properties of the mu-metal/ferrite that should be assumed in any future measurements. Since mu-metals properties in particular are sensitive to deformation, it is best to make this measurement in the form the sensor will be used.

Many of the applications require many material properties to be estimated simultaneously. This high dimensional property inversion is difficult and often requires a combination of many different approaches.

An n-unknown multiple frequency inversion without any hierarchical treatment or segmented field information. For example, on a pipe with no weather jacket, the unknowns may be selected as liftoff, pipe thickness, permeability, and conductivity. In some applications all four unknowns can be estimated independently. In others, one or of more be considered constant. In a configuration with a weather jacket, this can add the weather jacket conductivity, permeability, thickness and distance from the weather jacket to the pipe as unknowns.

A hierarchical approach can be used to increase numerical stability and accuracy of the multiple unknown inversion. Property effects can be systematically separated from one another by using specific frequencies to estimate the properties they are most sensitive to.

A segmented field approach with multiple sense elements and/or multiple drives may help increase measurement independence between near and far surface properties.

When using one segment of the sensor to provide information to other segments of the sensor, it may be necessary to use a numerical method to convert material signatures from one segment to the other due to differing sensor footprints. A specific application of this is the need to use near segments to correct far segments for weather jacket variations such as straps and overlap regions.

A sensor with both inductive and MR elements may allow for an individual sensor to operate effectively over a larger frequency range, taking advantage of the inductive sensor's sensitivity to the rate of change of the magnetic field at higher frequencies and the MR sensor's sensitivity to the magnetic field at lower frequencies.

Repeating scan at multiple lift-offs may increase measurement independence between various material properties. Similarly, a single scan can simulate multiple liftoffs by placing multiple drives at different heights relative to the sense element and alternating excitation between the two drives.

A 4-point-probe may be used separately to measure conductivity independent of other material properties Steel may need to be modeled as having a complex and/or frequency dependent and/or depth dependent permeability.

Analytical and numerical methods or some combination of the two can be used to correct for and accurately size local property variations. This includes but is not limited to weather jacket straps and overlap regions as well as pipeline localized defects.

Calibration can be performed in a number of manners including but not limited to air calibration, single or multiple point reference calibration, air and reference part calibration, air and shunt calibration, any number of more complicated calibration procedures.

The use of the cylindrical extension of the models provides the opportunity for a more complicated air calibration procedure. Modifying the radius of the sensor (or any other systematic change to a sensor that changes the sensors response in air) provides an independent air calibration point allowing for the estimation of the parasitics of the impedance instrument system without the use of a shunt. This can simplify the measurement procedure.

Complex Geometry Locations

In locations with more complicated geometries it may become more important to use techniques such as 2-D stationary arrays to reduce convective effects and take measurements at known distances away from the complicating geometry. Analytical and numerical models may be combined to more carefully account for the complicating geometries. The pipeline may be adapted with inspection ease in mind. Reducing the difficulty of the inspection process can be achieved by using lower conductivity-permeability-thickness product weather protection material as compared to aluminum or magnetic steel materials. Some suggested materials include but are not limited to stainless steel, plastic, polymer, fiber glass, carbon fiber composite, Kevlar, materials used in flexible armor.

Having thus described several aspects of at least one embodiment of this invention, it is to be appreciated that various alterations, modifications, and improvements will readily occur to those skilled in the art.

Such alterations, modifications, and improvements are intended to be part of this disclosure, and are intended to be within the spirit and scope of the invention. Accordingly, the foregoing description and drawings are by way of example only.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

In this respect, it should be appreciated that one implementation of the above-described embodiments comprises at least one computer-readable medium encoded with a computer program (e.g., a plurality of instructions), which, when executed on a processor, performs some or all of the above-discussed functions of these embodiments. As used herein, the term "computer-readable medium" encompasses only a computer-readable medium that can be considered to be a machine or a manufacture (i.e., article of manufacture). A computer-readable medium may be, for example, a tangible medium on which computer-readable information may be encoded or stored, a storage medium on which computer-readable information may be encoded or stored, and/or a non-transitory medium on which computer-readable information may be encoded or stored. Other non-exhaustive examples of computer-readable media include a computer memory (e.g., a ROM, a RAM, a flash memory, or other type of computer memory), a magnetic disc or tape, an optical disc, and/or other types of computer-readable media that can be considered to be a machine or a manufacture.

The terms "program" or "software" are used herein in a generic sense to refer to any type of computer code or set of computer-executable instructions that can be employed to program a computer or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A system for detecting damage in a hollow cylinder through an outer non-conducting layer which is further surrounded by a thin conducting layer, the system comprising:
   a sensor having an array of sensing elements and a drive winding, the sensor configured to be positioned outside of the thin conducting layer to sense the hollow cylinder through the non-conducting layer and the thin conducting layer;
   an analyzer operably connected to the sensor and configured to drive a current in the drive winding at a plurality of measurement frequencies and to measure a response of each sensing element in the array at each measurement frequency; and
   a processor configured to
      estimate at least one material property of the thin conducting layer from at least the response of the sensing elements of the array at a first measurement frequency among the plurality of measurement frequencies,
      estimate a spacing between the thin conducting layer and the hollow cylinder, and a wall thickness of the hollow cylinder from at least the response of the sensing elements of the array at a second measurement frequency among the plurality of measurement frequencies, where the second measurement frequency is a lower frequency than the first measurement frequency, and determine damage to the hollow cylinder based on the estimates.

2. The system of claim 1, wherein the processor is further configured to estimate a lift-off of the sensor from the thin conducting layer from at least the response of the sensing elements of the array at the first measurement frequency.

3. The system of claim 1, wherein the processor is further configured to identify regions of external and internal wall loss of the hollow cylinder using the estimated spacing between the thin conducting layer and the hollow cylinder and the estimated wall thickness of the hollow cylinder.

4. The system of claim 1, wherein:
the array of sensing elements is a first array of sensing elements;
the sensor further comprises a second array of sensing elements with a different gap to the drive winding than the first array of sensing elements;
the impedance analyzer is further configured to measure responses of each sensing element in the second array at a second plurality of measurement frequencies that may or may not be different than the first plurality of measurement frequencies, and
the processor is configured to utilize the responses from both the first and second arrays to determine damage.

5. The system of claim 1, wherein the analyzer is configured to drive the drive winding at each of the plurality of measurement frequencies sequentially and measure the responses at each sensing element simultaneously using a parallel architecture.

6. The system of claim 1, wherein the processor is configured to use assumed properties of the thin conducting layer if the estimated material property of the thin conducting layer indicates that the thin conducing layer has a conductivity-thickness product below a threshold, and to use the estimated material property of the thin conducting layer if the estimated material property is above the threshold.

7. The system of claim 1, further comprising a non-transient computer-readable storage medium operably connected to the processor, said storage medium having a precomputed database of sensor responses, and the processor is configured to generate the estimates by comparing the sensing element responses to responses stored in the precomputed database.

8. The system of claim 7, wherein the database stored in the non-transient computer-readable storage medium are responses precomputed based on a planar physics-based layered media model.

9. The system of claim 7, wherein the database stored in the non-transient computer-readable storage medium are responses precomputed based on a numerical method.

10. The system of claim 7, wherein the database stored in the non-transient computer-readable storage medium are responses precomputed based on a physics-based model that accounts for the cylindrical shape.

11. The system of claim 1, wherein the array of sensing elements is a first array and the sensor further comprises a second array of sensing elements having a same gap to the drive winding as the first but located on an opposite side of the drive winding as compared to the first array.

12. The system of claim 11, wherein the responses of the first and second array are used to correct for the effects of motion and to measure the velocity of the sensor relative to the hollow cylinder.

13. A method of operating the system of claim 1, wherein the hollow cylinder is a pipe, the non-conducting layer is an insulating layer surrounding the pipe, and the thin conducting layer is a metal weather protection, the method comprising:
calibrating the sensor;
positioning the sensor on the weather protection; and
operating the analyzer and processor to obtain sensing element responses at each of the plurality of measurement frequencies and to provide the estimates and determination of damage to the pipe.

14. The method of claim 13, where the processor outputs the determined damage to the pipe as an amount of internal corrosion loss and an amount of external corrosion loss at locations on the pipe.

15. The method of claim 13, further comprising:
moving the sensor along the pipe while repeatedly operating the analyzer to obtain sensing element responses; and
operating the processor to generate the estimates and provide an image of the pipe damage.

16. The method of claim 15, wherein positioning the sensor comprises aligning the array in the circumferential direction of the pipe, and moving the sensor along the pipe comprises movement in the axial direction of the pipe.

17. The method of claim 15, wherein positioning the sensor comprises aligning the array in the axial direction of the pipe, and moving the sensor along the pipe comprises movement in the circumferential direction of the pipe.

18. The method of claim 15, wherein the sensor is moved at a constant velocity, reducing the effect of magnetic convection on the sensing element responses.

19. The method of claim 15, further comprising recording velocity information of the sensor during the moving; and wherein operating the processor to provide estimates comprises utilizing the velocity information to correct for magnetic convection.

20. The method of claim 13, wherein calibrating the sensor comprises positioning the sensor in a non-conductive, non-permeable environment with the same curvature as if the sensor is positioned on the metal weather protection.

* * * * *